(12) United States Patent
Ribi

(10) Patent No.: US 7,776,371 B2
(45) Date of Patent: *Aug. 17, 2010

(54) METHODS AND COMPOSITIONS FOR PREPARING CONSUMABLES WITH OPTICAL SHIFTING PROPERTIES

(75) Inventor: Hans O. Ribi, Hillsborough, CA (US)

(73) Assignee: Segan Industries Inc., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/523,723

(22) Filed: Sep. 18, 2006

(65) Prior Publication Data

US 2007/0071680 A1 Mar. 29, 2007

Related U.S. Application Data

(63) Continuation of application No. 10/302,368, filed on Nov. 22, 2002, now abandoned, which is a continuation-in-part of application No. 09/892,018, filed on Jun. 25, 2001, which is a continuation-in-part of application No. 09/602,001, filed on Jun. 23, 2000, now Pat. No. 6,607,744.

(51) Int. Cl.
*A23L 1/27* (2006.01)
(52) U.S. Cl. .................... 426/87; 426/88; 426/250
(58) Field of Classification Search ............... 426/87, 426/88, 250, 268
See application file for complete search history.

(56) References Cited

U.S. PATENT DOCUMENTS

| | | | |
|---|---|---|---|
| 3,309,274 A | 3/1967 | Brillant et al. | |
| 3,999,946 A | 12/1976 | Patel et al. | |
| 4,339,240 A | 7/1982 | Patel et al. | |
| 4,737,463 A | 4/1988 | Bhattacharjee | |
| 4,847,066 A | 7/1989 | Honigs et al. | |
| 4,853,235 A * | 8/1989 | Tomomatsu | 426/93 |
| 4,859,538 A | 8/1989 | Ribi et al. | |
| 4,892,677 A * | 1/1990 | Preziosi et al. | 252/408.1 |
| 5,053,339 A * | 10/1991 | Patel | 436/2 |
| 5,085,801 A * | 2/1992 | Thierry et al. | 252/408.1 |
| 5,144,112 A | 9/1992 | Wyatt et al. | |
| 5,156,810 A | 10/1992 | Ribi et al. | |
| 5,176,905 A | 1/1993 | Ohno et al. | |
| 5,189,281 A | 2/1993 | Wyatt et al. | |
| 5,273,360 A | 12/1993 | Wyatt et al. | |
| 5,415,999 A | 5/1995 | Saul et al. | |
| 5,685,641 A | 11/1997 | Ribi et al. | |
| 5,788,375 A | 8/1998 | Parker et al. | |
| 5,918,981 A | 7/1999 | Ribi et al. | |
| 6,046,455 A | 4/2000 | Ribi et al. | |
| 6,607,744 B1 * | 8/2003 | Ribi | 424/439 |
| 6,866,863 B2 * | 3/2005 | Ribi | 424/439 |
| 2002/0034475 A1 | 3/2002 | Ribi et al. | |

FOREIGN PATENT DOCUMENTS

JP 61250080 A * 11/1986

OTHER PUBLICATIONS

Ma et al. Journal of the American Chemical Society (1998) 12:12678-12679.
Brown et al., eds. Photochromism in Techniques of Chemistry (1972) vol. 3.
Durr et al., eds. Photochromism; Molecules and Systems in Studies in Organic Chemistry (1990) 40.
Keum et al. Bull Korean Chem. Soc. (1995) 16:1007.
Levesque et al. Chem Materials (1996) 8:2843.
Consumable Dictionary.com Online. Internet accessed on Mar. 14, 2006. <http://dictionary.reference.com/search?q=consumable>.

* cited by examiner

*Primary Examiner*—Leigh C Maier
*Assistant Examiner*—Jonathan S Lau
(74) *Attorney, Agent, or Firm*—Bret E. Field; Bozicevic, Field & Francis LLP

(57) ABSTRACT

Ingestible compositions comprising a chromic change agent together with methods of making and using them are provided. The chromic change agent alternatively may be associated with the ingestible, such as a packaging material for the ingestible. In response to a triggering event, physical or chemical, the chromic change agent changes color to provide information as to the history of the ingestible, either prior or contemporaneous with use. Depending on the use, the color change agent may be reversible or irreversible. Various solid or liquid ingestible compositions are provided for determining ingestible temperature, storage temperature, user temperature, light exposure, pH change, hydration or solvation change, mechanical stress, and the like, particularly in comestibles. Of particular interest are polydiacetylene polymers that may be formulated to provide compositions having numerous different color transition triggering mechanisms. The invention is also related to other chromic change agents that may be incorporated into ingestibles.

26 Claims, No Drawings

METHODS AND COMPOSITIONS FOR PREPARING CONSUMABLES WITH OPTICAL SHIFTING PROPERTIES

CROSS REFERENCE TO RELATED APPLICATIONS

This application is a continuation of U.S. Ser. No. 10/302,368 filed Nov. 22, 2001 which is a continuation in part of U.S. Ser. No. 09/892,018 filed Jun. 25, 2001 which is a continuation in part of U.S. Ser. No. 09/602,001 filed Jun. 23, 2000, which disclosures are hereby incorporated by reference.

INTRODUCTION

1. Technical Field

The field of this invention is methods and compositions for preparing an edible consumable or ingestible comprising one or more chromic change agent that is safe for human or animal consumption that interactively modulates a color transition in the edible consumable or ingestible.

2. Background

Foods, beverages, medications and a variety of edible products with intrinsic color change properties can find a multitude of uses for manufacturers and consumers alike. They can be developed and marketed for entertainment purposes, such as graphics on the surface of food that change color, giving rise to a visual effect that is both pleasing and interesting for children. A variety of new food categories can be produced to contain the chromic material. Food producers are in need of new means to differentiate brands, extend product lines, advertise and promote, and create new product lines. Generally, food developers are limited to new flavors, colors, presentations, packaging, and combinations for product differentiation. Entirely new categories of foods, beverages, and medications can be created by introducing a new intrinsic property during processing.

Color changes may release or expose hidden messages which can be used for promotional or marketing purposes. Color changes can visually signal the consumer when the food is "done" to a satisfactory extent and safe to eat, or that the food is still in the process of being cooked. Color changes can be used to communicate optically with a cooking instrument telling the cooking instrument the level of doneness through a bar code change.

Color change foods can indicate to consumers or institutions that the food offered is sterile due to its color at purchase. Subsequent changes in color could indicate that the food has become stale or spoiled. Safe food storage temperatures can be indicated by the food or beverage directly where a color change indicates that the food was held at an inappropriate temperature for a period of time. The color change can be used to signal the timely release of a certain nutrient or flavor into the food. The chromic change can also be used to communicate the nature of food to be consumed. For example, chromic change agents can tell the consumer how "hot" a hot sauce really is, the fat content of certain foods, the level of carbonation in soft drinks, or the level of a biological or chemical in a food, such as caffeine or allergens.

Certain spices and other foods should be irradiated with high-energy sources to ensure that potential microbial contamination has been eliminated, thereby protecting the consumer. Foods containing a chromic agent that changes color upon irradiation can communicate to the consumer or the food processor that proper irradiation has taken place.

Relevant References

Colored food products on the market today involve the use of commercialized dyes combined with a capsule of waxes or other opaque matrices that mask the underlying dye. The dye molecules become visually exposed upon dissolving or melting of the encapsulating material. An example of releasing a dye into hot water involves Quaker Oat's Deep Blue Hot Oatmeal. An example of dissolving a coated dye into cold milk involves a version Nabisco's Oreo Cookie that releases a blue dye into milk when the cookie is dipped into the milk. An example using melting waxes to reveal an underlying color involves Kellogg's PopTarts where a white wax is coated over a colored sprinkle. When the pastry is heated the wax melts to reveal the color. An example of beverage additive is Kraft Food's Kool-Aid Magic Twists incorporating an entrapped dye that becomes revealed as the coating on the food color is dissolved. An example of a color change when a food product is eaten is FritoLay's Cheeto's Cheese Puffs, which release a dye into one's mouth when the product is wetted and chewed. An example of a chewing gum which turns one's mouth blue is Blue Mouth Chewing Gum from Creative Products Manufacturing. In each case a color is revealed by releasing or exposing a hidden dye and not an intrinsic chromic change that results from a molecular change in the chromic change agent itself.

References of interest include U.S. Pat. Nos. 4,859,538; 5,144,112; 5,156,810; 5,189,281; 5,273,360; 5,415,999; 5,685,641; 5,788,375; 5,918,981; and 6,046,455.

SUMMARY OF THE INVENTION

Environmentally responsive components are intrinsically associated with ingestibles, such as foods, beverages and medicaments, to be consumed as part of the ingestible, while providing knowledge of an informative or entertaining character. Specifically, physiologically acceptable chromic materials, e.g. polymerized polyacetylenes, are associated with the ingestible so as to be consumed by the user. The chromic material changes color in response to various environmental clues, such as temperature, pH, radiation, and physical stress, among others.

DESCRIPTION OF THE SPECIFIC EMBODIMENTS

Ingestibles are provided comprising a chromic material that changes color in response to environmental cues.

A variety of color change triggering processes can be used to cause the color change of chromic change agents depending on the type of chemistry involved, such as temperature, pH changes, changes in ionic strength, mechanical changes such as stress or pressure during mixing or contortion, chemical changes such as the addition of a second component, exposure to light for a photochromic effect, biochemical reactions such as binding pair interaction (e.g., an antibody-antigen interaction, a receptor-ligand interaction), solvent environment changes, hydration or dehydration, solvent changes, and enzymatic changes where enzymes in the food can induce a change. The color-indicating material can be processed directly into the ingestible, coated on the surface, released in a timely manner, or be made to be exposed through a discrete color change triggering process.

By ingestibles is intended compositions that are taken orally, even though they may not be digested. Therefore, ingestibles include foods, medicaments, toothpaste, mouth washes, gargles, swabs, and the like, where the food is introduced into the mouth and may then be rejected or may reside in the mouth for a limited period of time. Since foods are the primary application of the subject invention, foods are discussed as illustrative of ingestibles generally. The chromic materials are physiologically acceptable, particularly polymerized polyacetylenes, which can be incorporated with the ingestible during or after processing. Only a small amount of the chromic material need be incorporated, where the chromic material may be suffused through the ingestible, partially penetrate the ingestible or primarily be an adherent coating on the ingestible. The ingestible is porous or liquid, so that the chromic composition, by itself or in conjunction with an edible carrier, interpenetrates the ingestible, where the penetration may be throughout the ingestible, a limited depth into the ingestible, or into the surface to provide an adherent surface.

Polydiacetylenes as a class of ingestible chromic agents offer several advantages since they exhibit a broad range of beneficial characteristics. They have a large extinction coefficient showing a high color contrast, so that proportionally less chromic change material may be required to achieve an optical effect than materials such as entrapped dyes. Polydiacetylenes are organic and can be modified to create a wide range of permutations applicable to different chromic triggering mechanisms, ingestible applications, and processing methods. They can be structurally modified to have more than one intrinsic color change (e.g. blue-magenta-red or blue red-yellow). They can be modified to be compatible with the different food matrices (e.g., fats, aqueous, starch, protein, inorganic salts, sugars or the like). They can be made structurally inert such that they are odorless and tasteless, thus not affecting the foods to which they are added. The polymer form is a high molecular weight structure thereby, reducing its potential for adsorption during the digestion process. Polydiacetylenes are compatible with a variety of compositions used in the food industry for coatings and processing, making them amenable to existing processing methods without complete processing line redesign (e.g., solid food forms or liquid food forms). They can be made into stable forms making them good candidates for tolerating the stresses of production, shipping and storage.

Polydiacetylenic and other chromic change materials that undergo an intrinsic color change respond directly to a triggering event rather than simply releasing a color. A direct response chromic change has the significant advantage that the chromic agent itself can be engineered and designed to meet a broad and varied interest in the food, pharmaceutical and other relevant industries. In the case of polydiacetylenic materials, the chromic agent can be chemically enhanced with different substituents and functional groups for various applications while maintaining the intrinsic color change characteristics. The unique conformational change mechanism that polydiacetylenes undergo during a color-changing triggering event provides a unique means to match the material with food-based chemistries, food processing methods, and printing and application processes.

Since polydiacetylenic materials can be modified to change color to a variety of different optical triggering mechanisms, they have the additional advantage that they may serve as indicators or reporters for a variety of different monitoring processes of interest to the food and pharmaceutical industries and consumers. Examples of such monitoring processes include cooking temperatures, presence of toxic chemical or microbial contaminants, heavy metal, the presence of carcinogens, allergens that can cause an immediate deadly reaction if the food is consumed, food content (e.g. specific substances in food which can induce a color change event if present), DNA or RNA, various gene products or genetically engineered substances, food oxidation state, freshness, temperatures that the food may have been raised to during shipping and handling, whether certain foods have been irradiated according to specific guidelines, and the like.

Diacetylenic and polydiacetylenic compounds may be produced in a multitude of forms or substituents for compatibility and functionality with foods, beverages and medications. The diacetylenic group may be modified with lipid-like groups for solid phase or liquid phase compatibility, carbohydrates, sugars, polar and apolar groups, functional groups such as amines, carboxylic acids, alcoholic groups, esters, amides, charge complexes, aliphatic groups, ethers, polyethers, amino acids, proteins, nucleic acids, mesogenic side chains, sulfhydryl groups, block co-polymers and other groups which may be used to create specifically desired characteristics. Compositions may be prepared having up to about 20 weight % of the polydiacetylenic polymer for coating, which compositions further comprise carbohydrates, lipids or other physiologically acceptable composition.

The diacetylenic compounds or chromic agents present, whether monomers or polymers, in the composition added to the ingestible will generally be present in at least 1 weight %, more usually at least about 5 weight %, and may be 75 weight % or more, usually being not more than about 60 weight %.

Diacetylenic monomer chemistries: Classes of photochromic, thermochromic, hydrochromic, lipochromic, and physiochromic polymers can be made from a variety of organic diacetylenic monomers including short chain molecules with no side chains or substituents, short chain molecules containing one or more functional groups and aliphatic monomers that vary in length from 10 carbon units to 50 or more carbon units with or without various functional side chains or substituents. Molecules can be hydrophobic or hydrophilic depending on the desired application. They can be neutral or charged in order to create a desired intermolecular or intramolecular effect. The molecule can be non-polar, mono-polar, or multi-polar. Diacetylenic monomers can be symmetric or asymmetric. For food grade applications, the monomer and subsequent polymer molecules can contain food compatible groups including sugars, lipid chains, carbohydrate moieties, amino acids, peptides, proteins, complex proteins, effector groups, esters, alcoholic groups, amides, carboxamides, dextrans, heterocyclic substituents, acids, lipids, detachable nutrient groups, such as vitamins and nutraceuticals, catalytic groups such as enzymes, chelating groups, nucleotides, food colors, emulsifier groups, or the like.

Side chains and substituents may be chemically modified for use with a variety of different foods. The hydrophobic or hydrophilic nature of the chemical compound can be adjusted to create compositions more or less compatible with fatty foods, carbohydrate-based foods, meats, dry foods, cereals, baked goods or the like.

The diacetylenic monomer will be a lipid mono- or dicarboxylic non-oxo carbonyl monomer or derivative thereof, so that acid, esters, or amides may be employed, a mono- or diol, ether or ester thereof, where the acid may be organic or inorganic, e.g. phosphate, an amino or derivative thereof, where the derivative may be an organic substituent such as an acyl group, an aliphatic group, an aromatic group, a heterocyclic group, etc. The substituents at the termini will have from 0 to 30, more usually 0 to 20 atoms, which will usually be carbon, oxygen, nitrogen, sulfur and phosphorous. The acid portion of the molecule (or underivatized portion) will generally range from 5-30, more usually 12-30, carbon atoms and the diacetylene groups which will be in conjugation, may be situated symmetrically or asymmetrically in the molecule. Thus, the flanking alkylene groups may be the same or different in a molecule, where the temperature transition of the polymer will depend upon the chain length of the monomer, whether the diacetylene groups are symmetrical or asymmetrical, and the degree of difference between the length of the flanking regions, whether one uses a single monomer to form a homopolymer or two or more monomers, usually not more than four monomers, to form a co-polymer, and whether the chains are substituted or unsubstituted, as well as the nature and degree of substitution. Particularly, halogen substituents, e.g. fluorine, chlorine and bromine, may be present to enhance the upper temperature limits possible with the subject compositions, ranging from a single substituent to persubstituted. The temperature range which is attainable using the various diacetylene monomers will range from about 25-300° C., usually not exceeding 200° C., more usually from about 25-200° C. For the purposes of this invention, the range of interest will be from about 30-200° C., more usually from about 35-200° C., and particularly from about 35-150° C.

For the most part, the diacetylene monomers will have the following formula:

$$R(CH_2)_n(C≡C)_2(CH_2)_mY \quad (1)$$

wherein:

Y is $COX^1$, amino (including substituted amino, e.g. alkyl substituted amino of from about 1-6 carbon atoms), oxy having from 0 to 6 carbon atoms, thio of from 0 to 6 carbon atoms, cyano, halo, etc.;

m and n are at least 1 and total 8-25, preferably n is at least 2, more preferably both m and n are at least 2;

R is H or Y; and

X and X' may be the same or different, usually the same, may be any of the groups indicated above, generally being H, OH, OT, where T is of from 1-8, usually 1-6 carbon atoms having from 0-(n−2) substituents, wherein n is the number of carbon atoms and the substituent may be oxy, amino, halo, thiol, etc, usually aliphatic, e.g. hydroxyalkyl, and aminoalkyl; or $NT^1$, $T^2$, wherein $T^1$ and $T^2$ are the same or different, usually the same and will have from 1-8, usually 1-6 carbon atoms, the total number of carbon atoms of $T^1$ and $T^2$ usually not being greater than about 6 and each having from 0-(n−2) substituents as described above, particularly oxy, one of $T^1$ and $T^2$ may be unsubstituted or substituted amino (hydrazino), where the substituents will come within the definition of $T^1$, polyalkyleneoxy, wherein alkylene is of from 2 to 3 carbon atoms and may have from 2 to 50 units; or two Y's may be taken together to form a divalent linking group of from about 2 to 2,000 daltons, which will usually be 2 T's taken together (T's include T and $T^1$). Monomers can be used individually and in pure form. The position of the acetylenic groups may be symmetrical or asymmetrical in the molecule.

Of particular interest are monomers, such as 10,12-tricosadiynoic acid (C23) or 10,12-pentacosadiynoic acid (C25), which can be used independently during processing and production to achieve a lower sensitivity to ultraviolet irradiation (254 nm) or either compound may be added in a percentage to the other to sensitize the mixture to make the mixture far more sensitive to ultraviolet irradiation. 0.01-50% by weight of C25 can be added to C23 to make a mixture that polymerizes 50% or more quickly and achieves a much darker blue appearance after polymerization. More usually, 0.1 to 30% C25 is added to C23. Typically, 1 to 20% C25 is added to C23. Formulation variations along with ultraviolet irradiation times can be used to create different thermochromic temperature settings. Combinations of formulations can be used to achieve a variety of visual effects upon temperature triggering including patterns such as text, characters, images, symbols, trademarks, brand identity marks, messages, icons, logos, artistic designs or decorative designs. Patterns may appear to change non-uniformly to create visual imagery such as the appearance of movement in a stationary picture.

The general structure of a diacetylenic monomer that is polymerized to become a polydiacetylenic chromic change agent consists of a diacetylenic unit with appending side chains on each end of the diacetylenic unit $$A(CH_2)_n\text{—}≡\text{—}≡\text{—}(CH_2)mB \quad (2)$$

The corresponding polydiacetylenic unit capable of undergoing a chromic change is a continuous ene-yne structure with $A(CH_2)n$ and $(CH_2)mB$ each as side chains attached to an individual ene-yne unit:

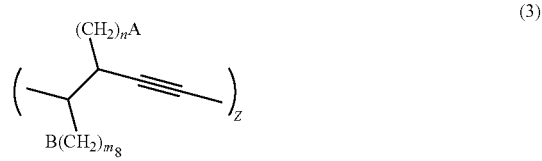

(3)

where Z represents the number of repeating units along the polydiacetylene backbone. Z can range in number from 2 to greater than 100,000. Usually Z will vary from 5 to 10,000. Typically Z will be between 10 and 1,000 units.

The number of methylene units n and m may be increased or decreased depending on the application of interest. Increasing the number of methylene units can have dramatically different effects on the resulting chromic triggering mechanisms. Altering the substituents A and B can have the effect of sensitizing, tuning or optimizing a particular chromic triggering mechanism in the chromic change agent. The composite structural features of an ingestible chromic change agent can be related to both the chromic change mechanism as well as the degree of responsiveness or non-responsiveness of the agent to a triggering event. Illustrative examples of chromic agent color change mechanisms and enabling structural features are summarized below but are not intended to limit the scope of possible mechanisms or structural permutations.

Photochromic agent color changes: The primary enabling feature for a diacetylenic material to be photopolymerizable such that exposure to ultraviolet light (254 nm) results in the formation of a color formation is the ordered crystal packing state of the monomeric diacetylenic unit. A, B n, and m must be balanced such that diacetylene crystals are aligned and can be topochemically polymerized. Typically A and B should be of a molecular size and structure to promote and not inhibit crystal packing or sterically restrict the diacetylenic units from packing close enough to each other in a crystal lattice as to restrict ene-yne bond formation to occur between units. A and B can be similar or dissimilar in structure. A and n can be paired to comprise an alkyl chain and give the molecule favorable hydrophobic-hydrophobic interactions for inducing good crystal packing. B and m can comprise an identical alkyl chain to A and n to give the photochrome a wax-like characteristic. In contrast, m can be between 1 to 20 units while B can be a simple hydrophilic head group such as an alcohol or amine. B can be more complex such as a carboxylic acid or amide linkage. Amine, amide, and carboxylic acid groups (B) paired with alkyl chains (A/n) make excellent ultraviolet photochromic candidates.

Short chain lipid-like compounds, where n=3, A is a methyl group, m=3 and B=COOH (see formula (3), above) form photochromic compounds that turn red at room temperature when exposed to ultraviolet (254 nm) light between 0° C. and 30° C. Long chain lipid-like compounds, where in combination n is between 4 and 20, A is a methyl group, m is between 2 and 20 and B=COOH form photochromic compounds that turn blue when exposed to ultraviolet light (254 nm) from as low as 0° C. to as high as 100° C.

Symmetric compounds where the diacetylenic group is in a fatty acid form and is dimerized by bridging each fatty acid group through an amide linkage with ethylene diamine or 1,4-diaminobutane make excellent candidates for photochromic agents due to their facile crystallization and polymerization characteristics.

Mechanochromic agent enabling features: Mechanochromic agents can be similar in structure to photochromic agents. A good crystalline matrix of the monomeric diacetylenic moiety is first formed followed by ultraviolet polymerization (254 nm). For mechanochromic triggering, it is desirable to start with a highly ordered blue polydiacetylenic polymer. Mechanical perturbation subsequently changes the blue form of the polymer to the red form. Other chromic changes such as conversion of the blue or red polymer form to a yellow form are also possible to achieve through intense and continued perturbation. Since only a mechanical stress such as rubbing, sheering, compressing, or similar physical means is required to cause a chromic change in the chromic agent and not a specific chemical reaction, the mechanochromic molecular structure has few limitations.

The structure can be a simple alkyl chain, a fatty acid, an ester, an amide, a carbonate group, a thiol, an ether group, a polyethylene group, a sugar, a carbohydrate, an amino acid or a variety of other groups that do not adversely affect a mechanically induced triggering event. The ease of inducing a mechanochromic change is dictated by the selected structure. Rigid crystal structures with a high degree of structural integrity of the mechanochromic polymer require a higher level of mechanical perturbation to induce a chromic change as compared with loosely packed crystal structures with weaker intermolecular interactions. For example, 5,7-hexadecadiynoic acid (16 carbons in length) requires little mechanical pressure to induce a chromic change in the polymer whereas 10,12-pentacosadiynoic acid (25 carbons in length) requires several times more mechanical pressure to induce a chromic change. Typically, the shorter the hydrocarbon chains (n and m less than 5) embedding the diacetylenic polymer the less mechanical stress required to change its color. Weakly interactive head groups or side chains such as esters groups (B) can be used to reduce the mechanical stress required to induce a chromic change whereas strongly hydrogen bonding head groups such as multiple amides increase the amount of stress required to induce a change.

The degree of polymerization (Z) can play an important role in dictating the mechanical forces required to induce a chromic change. Short repeating units, caused from mild polymerization (e.g. where Z is 3-10 units), can result in less required force needed to induce a change. Longer repeating units, caused by extensive ultraviolet polymerization, (e.g. where Z is from 50 to over 1,000), can result in requiring significantly greater forces to induce a chromic change.

Thermochromic agent enabling features: A primary feature dictating a thermally induced chromic change is the melting transition of side chains appended to the polydiacetylenic structure. Similar to the mechanochromic example, shorter, more weakly interactive side chains typically require lower heat levels to induce a chromic change. Longer, more strongly interactive side chains typically require higher heat levels. In the case of thermochromically induced changes, it is desirable to utilize side chain substituents most affected by temperature changes. Lipids, waxes and other hydrocarbons can be used. In combination with side chain substituents, more strongly or weakly functional groups may be used to adjust the thermochromic transition.

Ester groups, for example, exhibit weak intermolecular interactions and are useful in lowering the thermochromic transition temperature, whereas amides exhibit strong hydrogen bonding interactions between adjacent repeating units and find use to raise the thermochromic transition temperature and facilitate a reversible thermochromic reaction. Sugar molecules exhibit a high degree of intermolecular hydrogen bonding and can be used to synthesize high temperature thermochromically reversible ingestibles (B) whereas polyethylene oxide substituents can be used as substituents (B) to synthesize lower temperature irreversible compounds. Permutations of the hydrocarbon chain lengths (n and m) appending the diacetylenic unit can be used to fine-tune the desired temperature change setting.

The degree of polymerization (Z) also plays an important role in dictating the temperature at which the chromic change will occur. Short repeating units, caused from mild ultraviolet polymerization (e.g., where Z is 3-10 units), can result in lower thermochromic transition temperatures. Longer repeating units, caused by extensive ultraviolet polymerization, (e.g. where Z is from 50 to over 1,000), can result in a significantly higher thermochromic transition temperature.

The compounds used to react with the carboxyl groups may be selected in relation to the ingestible to be modified. Thus, the groups may be chosen to make the polyacetylenes more compatible with the ingestible, using polar compounds to enhance compatibility with polar ingestibles, non-polar compounds to make the polyacetylenes more compatible with lipid compounds, solubilizing groups which provide for solubility or dispersibility, and the like. Certain photochromic materials can undergo a second color transition upon high heat (greater than 200° F.) from a red color to a yellow color and then reverse colors upon cooling back to room temperature. Among such materials are the dual chain glutamate diacetylene containing lipids. Mono-amide glutamate lipids and tri-amide glutamate lipids can be used alone or in combination to achieve similar effects at lower temperatures. For example, the molecule can be modified to have strong hydrogen bonding characteristics that cause strong intermolecular interactions between monomers along a polymer chain and exert a strong ordering characteristic along the chain. Strong intramolecular or interpolymer chain hydrogen bonding helps to stiffen and order the polymer backbone. Heading or perturbing the backbone cause a stochastic conformational change along the polymer that results in a color change from a highly ordered blue structure to a red disordered structure. Cooling or reversing conditions allows the intermolecular or intra-polymer chain hydrogen bonding interactions to dominate and re-order the polymer chain to an ordered blue structure. Among such materials are single chain lipids containing one or more amides for promoting intermolecular hydrogen bonding. For example, acetylated ethylene diamide-10,12-triconsdiyneoic amide contains two internal amide linkages along a single chain compound. Alternatively, dual chain lipids containing a mono-, di- or triamide glutamate head group can be used. In addition carboxylic acid lipids where the diacetylenic back bone is in close proximity with the head group (1-4 carbon atoms removed) have a large influence over the polymer structure and can exhibit reversibility (e.g. 4,6-heptadecadiynoic acid) at moderate temperatures (68° F. to 130° F.). Reversible thermochromic materials can be made using glutamic acid with two chains of 10,12-tricosadiynoic acid to form a dual chain glutamate lipid. Dual chain glutamate lipids exhibit a high degree of thermochromic reversibility due the interlocking nature of the microcrystalline structure and/or their hydrogen bonding characteristics. Generally there will be from 1 to 10, more usually from about 1 to 8 hydrogen forming groups in a repeating unit of the polymer, such as amide, hydroxy, keto, amino, etc.

A chemical/structural balance between carbon chain length, position of the diacetylenic group along the carbon chain, hydrogen bonding due to the amide linkage, and head group structure can be achieved in the chromic change agent to give it characteristics of reversibility, food compatibility, processing ease, color change mechanism, stability, and other factors beneficial to use as an ingestible.

Diacetylenic forms of the chromic agent can be made into a high temperature reversible material by creating a dual amide symmetric compound where two long chain fatty acids (10,12-pentacosadiynoic acid) are bridged by an amide linkage by 1,4-butane diamine. The resulting material forms a plastic/wax-like polymerizable material which remains dark blue until it is heated above 150° C. Halogenating the even longer chain fatty acids along their methylene units can further raise the triggering transition temperature to greater than 300° C.

Depending on the type of application, it may be desirable to have an irreversible thermochromic or physiochromic event or a reversible event. Hot liquids containing a reversible thermochromic material, for example, can be made to turn red at a high temperature and back to blue at some intermediate or room temperature. Upon reheating, the liquid would turn red again.

Cereals containing a low temperature reversible chromic material can be red at room temperature and change to blue upon addition of cold milk. An irreversible thermochromic material can be used to show a pattern change in a solid pastry indicating that the pastry was indeed heated to a certain temperature to reveal a message or picture which stays the same even after cooling. Single chain monomers such as 10,12-tricosadiynoic acid can be polymerized to form an irreversible thermochromic property.

For lower temperature applications such as visualizing a color change when a food is brought to room temperature or above, it is desirable to have a thermochromic compound which responds immediately to an ambient room temperature. 10,12-tricosadiynoic acid or 10,12-pentacosadiynoic acid can be converted to the methyl ester form to create materials which change color from a deep dark blue to irreversible bright red, at about 80° F. These can be useful for indicating that certain foods, which should be stored at less than room temperature, have been raised or heated to higher than room temperature. For example, in some cases such as certain medications, dairy products or foods, it is desirable to store them at room temperature or below and keep them from being raised even slightly above room temperature. In these cases, it may be desirable to incorporate a thermochromic material, which tells consumers that the product has at one time been held at an undesirably high temperature and should no longer be consumed. It may be advantageous to have the thermochromic material in direct contact with the consumable medication or food and not with packaging, so that no false indications are made, and precluding expensive items from being disposed of inappropriately. Shorter hydrocarbon chains attached to the diacetylenic backbone can also be incorporated to reduce the energy or impact required to trigger a chromic transition. A balance between the hydrogen bonding, Van der Waals interactions, charge-charge interactions, hydrophobic-hydrophilic interactions, can be achieved to produce the desired type and situation for color changing ingestibles.

Hydrogen bonding functional groups attached to monomers can be used to influence the chromic properties of corresponding polymers. Tightly hydrogen-bonding groups can increase the energy required for the chromic material to change color. Reducing the hydrogen bonding capabilities of the chromic material can be used to reduce the energy or degree of change in environment to cause a color change. Hydrogen-bonding groups include polar atoms, such as oxygen and nitrogen, to which the hydrogen is bound. Hydrogen bonding can be structured between individual chromic molecules or between chromic molecules and surrounding carrier materials with which they are in association.

Of particular interest are thermochromically revisable monomers such as N-ethanol-hexadeca-5,7-diyneamide and N-propylamineeicosa-5,7-diyneamide. These compounds when polymerized with ultraviolet light (254 nm), become deeply magenta colored at room temperature. When the polymers are raised above room temperature they become red/orange and when they are chilled below room temperature, they become a deep purple/blue color. The thermochromic transition of N-ethanol-hexadeca-5,7-diyneamide is approximately 5° C. lower than N-propylamine-eicosa-5,7-diyneamide. The lower temperature triggering transition was achieved by using an ethanolamine head group rather than a propylamine head group and using a shorter 16 carbon chain rather than a longer 20 carbon chain. N-ethanol-hexadeca-5,7-diyneamide finds application to color changing cereals where at room temperature the cereal will appear magenta/red and turn blue when cold milk is added to the cereal. N-propylamine-eicosa-5,7-diyneamide finds application to coatings on cookies where at room temperature the cookie appears a dark magenta. When the cookie is touched, raising its temperature above room temperature, the cookie appears red. When the cookie is dipped in cold milk, the cookie appears dark blue/purple.

High-temperature reversible chromic agents find multiple uses both indicators that foods have been raised above a safe cooking level (e.g., one color will appear above 160° F.) and then subsequently as indicators that foods have been cooled to a level that makes them safe to eat without burning tissue in the mouth (e.g., the original color will reappear near 110° F.).

Chemical changes such as these provide for wide range of latitude to modify the chromic agent for a particular triggering range and product application. Food or other ingestible products often have discrete requirements such as shipping, storage, level of contaminants, acceptable moisture content or the like.

Irreversible color changes in polydiacetylenes can be introduced by eliminating or reducing the intermolecular or intrapolymer chain hydrogen bonding characteristics. For example, the polydiacetylenic molecule can be a pure hydrocarbon structure without substituents, an ester or have other relatively non-interactive groups. Additionally, the triggering temperature can be dramatically reduced and made irreversible by using short carbon chains such as 5,7-dodecadiynoic acid amidated with 2-(2-aminoethoxy)ethanol. The material is an oil at room temperature and will only polymerize at −10° C., where a blue polymer can be formed by ultraviolet irradiation (254 nm). Raising the temperature above −10° C. causes the material to irreversibly turn red/orange. Materials such as these can find use in low temperature food applications.

Irreversible color changes are important to ingestibles containing them when it is desired to observe a color change at a certain temperature level and it is desired to maintain "memory" of the temperature level achieved at a given time or location. It is convenient to use irreversible thermochromic color change in polydiacetylenes during a temperature increase, converting the blue form of the color to a red form. For example, a thermochromic message can be revealed on a toaster pastry and the message is permanent until the pastry is ingested.

Extended triggering conditions can be achieved in polydiacetylenic compounds by creating unique structures including attachment of constituent moieties such as sugars, amine acids or peptides, DNA or RNA, polyether groups, binding pairs, or organic groups which can dominate the material's characteristics. Maximum temperature triggering ranges attainable can be extended to −30° C. or below to greater than 350° C., usually not exceeding 300° C. and not below 25° C., and more usually from between −20° C. to 250° C. For the purpose of this invention the range of interest will be from −15° C. to 225° C., and particularly from −10° C. to 200° C.

Likewise, the substituents can be added to provide for other means to disrupt or order the polymer structure and thereby cause a reversible or irreversible color change in the polymer backbone, as described below.

Hydrochromic/solvatochromic agent enabling features: An important feature dictating the hydrochromic/solvatochromic nature of the chromic agent is the ease of degree to which the material can be effectively hydrated of solvated by a surrounding medium. The mechanism for inducing a hydration or solvation change can be accomplished either by affecting individual substituent side chains or by hydrating/solvating complete layers adjacent to each other in the crystalline lattice. As with other chromic change mechanisms, the ease or difficulty of inducing a chromic change can be dictated by the integrity of crystal packing and the strength of intermolecular side chain interactions.

Good hydrating side chain groups A and B include alcohols, polyethers such as polyethylene glycol terminated with an OH group, surfactant groups or the like. Solvation-induced chromic changes, where polar aprotic solvents such as acetone are used as the triggering agent, are effective when the side chain substituents are easily solvated with acetone. For example, n and m can be low in number (e.g. 1 to 3 units) and the head group can be a like kind substituent such as a ketone or ester. Water-induced chromic changes are facilitated when both the intermolecular interactions between side chains and the intercrystalline interactions between layers of the crystal lattice are affected by water. It can be desirable to use symmetric compounds where A=B and n=m and both A and B are groups that are easily hydrated as well as groups which permit intercalation of water between layers in a crystal.

Mono- or multiple alcoholic groups can be introduced to promote interaction with hydrating or solvating solutions. Solvent or hydrochromic color changes are particularly attractive when combining dry ingestibles with wet or moist ingestibles. For example, adding milk to cold cereal, dipping cookies or crackers in milk, adding crackers to soup, pouring liquid syrups on breads or pancakes, adding salad dressings to salads, or the like, can be the trigger for a color change.

In addition, hydrochromic/solvatochromic effects can be used in unique ways to propagate a color change along a surface. As hydration occurs along an absorbent layer and the moisture migrates, a blue form of the polymer sensitive to solvation or hydration will turn the disordered red of the polymer to the ordered blue form. Messages or graphics can be visualized sequentially to create time-resolved graphical changes.

Ethylene glycol or polyethylene glycol groups can be attached to the monomeric material to alter the solubility with different food types or help emulsify the monomeric chromic agent. Ethylene glycol linkers can range from a single ethylene oxide unit to 50 units. More typically, ethylene glycol linkers range from 2 to 20 units and most conveniently from 3 to 6 units. The number of units can be changed depending on the desired level of hydrophobic or hydrophilic nature for the resulting molecule.

Standard hydrochromic/solvatochromic indicating groups can be attached in positions A and/or B to endow the base chromic change agent with moisture-indicating properties.

pH sensitive and ionochromic change agent enabling features: It is desirable to attach pH or ion sensitive substituent groups to the base molecular structure such that a change in solution pH or ionic strength in the surrounding medium can induce a chromic change in the polydiacetylenic backbone. As with other chromic change mechanisms, the ease or difficulty of inducing a chromic change can be dictated by the integrity of crystal packing and the strength of intermolecular side chain interactions. For example, groups that respond to ionic strength such as a carboxylic acid can be used at positions A and/or B. It is desirable to use shorter side chain lengths (e.g., n and m less than 4) in order to facilitate a higher degree of molecular mobility. A dicarboxylic acid where A and B are both COOH and n and m are both 1 to 3 are of interest as ionochromic constituents since both ends of the molecule are affected during a triggering phase.

Groups susceptible to protonation or deprotonation or acid-base reactions are of particular interest. For example, A and/or B can be a primary amine, secondary amine or the like. Changing the surrounding medium from a neutral pH to an acidic pH can be used to cause a chromic change in the medium. When A and/or B is an organic acid such as a mono or dicarboxylic form, treating the medium with a basic solution may induce a chromic change in the agent.

pH sensitive groups, e.g. bases and acids such as a hydrazide or a free amine group, can be attached to the head group of a lipid or hydrocarbon moiety to invoke a pH-triggering response from the blue form of the polydiacetylenic polymer to a red form of the polydiacetylenic polymer. Ethylene glycol or polyethylene glycol groups can be attached to the monomeric material to alter the solubility with different food types or help emulsify the monomeric chromic agent.

Ethylene glycol linkers can range from a single ethylene oxide unit to 50 units. More typically, ethylene glycol linkers range from 2 to 20 units and most conveniently from 3 to 6 units. The number of units can be changed depending on the desired level of hydrophobic or hydrophilic nature for the resulting molecule.

Standard pH-indicating groups can be attached in positions A and/or B. Indicators specific to a particular pH unit are of interest since they may find use as ingestibles to monitor saliva pH. Ionophore-sensitive groups can be attached in position A and/or B to endow the base chromic change agent with ion-selective properties.

Chemochromic and biochromic agent enabling features: It is desirable to attach chemically or biochemically sensitive and/or selective groups to A and/or B to give the chromic agent specificity to certain chemical constituents in an ingestible matrix. As with other chromic change mechanisms, the ease or difficulty of inducing a chromic change can be dictated by the integrity of crystal packing and the strength of intermolecular side chain interactions.

Examples of chemically selective groups can include caged compounds, chelating compounds, crown ether groups, peptides, DNA or RNA fragments, transition state analogs, binding pair members, or the like. Groups A and/or B can be more or less selective depending on the ingestible application. The chromic agent can be made more or less sensitive to chemical or biochemical triggering by increasing or decreasing n and m, respectively; shorter chain lengths typically require of lower concentrations of the chemical or biochemical to induce a chromic change, whereas longer chain lengths generally require higher concentrations of the chemical or biochemical required to induce a chromic change.

Formulations and compositions: Monomeric or polymeric chromic change materials can be combined with a carrier material to form a composition which makes it possible for it to be applied to and/or adhered to foods. Carrier materials can range from a simple aqueous solution to complex mixtures containing different emulsifiers, flavors, or foodstuff. Constituents such as oils, lipids, waxes, sugars, salts, lectins, agglutinins, protein matrices, carbohydrate matrices or the like can be combined alone or together with an unpolymerized agent or polymerized agent to give the agent the properties necessary for transfer to, adherence with, or stability on a food type.

Carrier materials suitable for printing can include aqueous solutions or pastes, which are applied and dried more slowly. Alternatively, the solution can contain an ethanol base, which can be dried more quickly. The carrier for printing can contain any food compatible composition.

Carrier materials suitable for extrusion can contain thickening substances to give it the consistency for rapid extrusion and pattern formation on the food surface of interest. Starches, methylcellulose, but pastes, dextrins, polydextrins, protein pastes, sugars, dried gelatins, rice papers, doughs, frostings, sugar-based papers, edible inks, edible waxes, ingestible polymer substrates, caramelized sugars, or the like can be used for a support surface to which the chromic agent can be applied. Thickened carriers provide for the ability to form three dimensional structures such as overlaying lines or patterns, that can enhance the contrast for the thermochromic or physiochromic color transition. Carriers suitable for lamination can include substances that provide for stable layers to be applied to the food of interest.

Binding agents can be used to integrate more or less of the chromic material with a particular food type. In most cases, it is desirable to bind the chromic material tightly to the food so that the material stays visibly in contact with the particular part of the food portion it is initially on and that the material does not slough off into a surrounding liquid or rub off on any packaging materials. Binding agents can include sugars, carbohydrates, proteins, methyl cellulose, and other materials commonly used to bind food colors, coatings, frostings, sprinkles and the like. The binding agent can be co-mixed with the chromic material, coated after application of the chromic material to form a protective layer, or used in combination with both the food and the chromic material.

Various traditional, inactive ingredients can be used to co-mix, pre-color or adhere the chromic agent to a support surface on the consumable product including: hydroxypropyl cellulose, hydroxypropyl methyl cellulose, microcrystalline cellulose, starch, red iron oxide, magnesium stearate, titanium dioxide, talc, colloidal silicon dioxide, polyethylene glycol, various synthetic polymers, Yellow 10 dye, carnauba wax, corn starch, sodium starch glucolate, or the like. These various additives are conventional and will be present, when employed, in a range of from about 0.1 to 95 weight %.

Configurations of application for chewable foods: The chromic material, such as diacetylenes, need to be in a microcrystalline phase in order to polymerize to the chromic material. Therefore, if the diacetylenes are to be mixed with other components that adversely affect the formation of the microcrystalline phase, the diacetylenes will normally be prepolymerized before formulation. Solution phase chromic material or monomer can be applied to a chewable food surface, dried and then polymerized. Liquid phase monomer can be polymerized if in a colloidal/crystalline form, applied to a solid food surface, and dried. Solid microcrystalline monomer can be admixed with food carriers, applied to a solid food surface, and then polymerized. Solid microcrystalline monomer can be first admixed with a food carrier, polymerized, and then applied to a food surface. Solid microcrystalline monomer can be first polymerized, admixed with a food carrier, and then applied to a food surface.

The solid surface of the food may be processed to accept the monomer or chromic material. In many cases, if the food surface is too porous the monomer or chromic material will dissipate into the interstitial spaces below the surface, rendering it unavailable for visualization. Solid food surfaces can be prepared for accepting the monomer or chromic material by modification of the food composition or coating the surface with a composition, which seals the food surface. In either case, application of the monomer or chromic material to the food surface will provide for a means to keep the material on the surface and visible. Illustrative of such situations are sugars, proteins, digestible celluloses, methylcellulose, polydextrins, digestible waxes and gums, which can also be used to create a smooth hydrophobic barrier for even coating of the physiochromic agent.

Structures containing the physiochromic agent can be created which come in contact with the food type of interest. The structures themselves can be compatible with food and can be made with digestible components or can be made of material that is certified for contact with food but not meant for consumption. Structures can be labels, part of the package, an insert in the package, paper rings, tabs or the like. The structures can be printed with the physiochromic material in a way in which the structure can interact with the food. For example, the structure can be an adherent label containing a thermochromic form of the agent. The adherent label can be adhered to a food type meant for heating. When the food is heated, the thermochromic agent will change color. If the label structure is edible, it can remain in contact with the food type and be consumed along with the food. If the structure is safe for food contact but not edible, it can be part of a packaging material or removed prior to consumption.

The monomeric or polymeric form of the chromic agent can be fused or admixed into foods or medications. For example, a polymerized liposomal or colloidal form of polydiacetylenic material can be processed with gelatin to produce a thermochromic form of desert gelatin. At refrigerator temperatures (40° F.), the gelatin could appear dark blue. When raised to room temperature (68° F.), the gelatin would turn bright red/orange. Alternatively, a polymeric chromic agent could be cast into a throat lozenge. A chromic agent that undergoes a temperature transition from dark blue to red/orange at 100° F. could be employed to help a consumer determine if they have a fever. Usage of the lozenge would indicate to the consumer that they have a low grade fever if the lozenge turns red/orange. The consumer could also examine his tongue to see if either a red or a blue color has come off the lozenge. Blue would indicate no fever and red/orange would indicate a low-grade fever. Similarly, chromic change agents can be incorporated in tablets, pills or other medications formulated to be taken by a sick patient, and can indicate the presence of a fever by a color change, which remains with or comes off the medication.

The thermochromic material can be patterned alone or in combination with food-based inks to create bar codes. Bar codes can be utilized in connection with cooking where the cooking system, equipped with a bar code scanner, can measure a change in the bar code as the code is exposed to high temperatures. Bars on the code can be made to change color when one or more temperatures are achieved. The optical density change in a given bar will result in a prescribed change and interpreted by the measuring system to indicate a specific temperature. The bar code can indicate doneness or in process cooking. The bar code can be printed directly on the solid food type or on the food packaging. This allows the bar code and bar code reader to be used as a temperature measure device.

Methods for triggering color change: The chromic change can be tailored to match a desired effect or outcome in a particular food or ingestible. Color change triggering processes can include temperature, pH changes, changes in ionic strength, mechanical changes such as stress or pressure during mixing or contortion, chemical changes such as the addition of a second component, exposure to light for a photochromic effect, biochemical reactions such as binding pair interaction, solvent environment changes, hydration or dehydration, solvent changes, and enzymatic changes where enzymes in the food can induce a change. The methyl or ethyl ester of 10,12-tricosadiynoic acid or 10,12-pentacosadiynoic acid is made by standard esterification in methanol or ethanol respectively. The ester compound can be applied to foodstuffs, crystallized and then polymerized at or below room temperature.

Physiologic changes in pH, ionic strength, or hydrogen bonding agents can be used to alter the state of the chromic material, which may be induced by finger touch or contact with saliva. Saliva is relatively acidic and can be used to induce an acidic environment which can cause a chromic change in foods containing the chromic material. The dark chromic material is extremely sensitive to thermal contact and changes color immediately at 70° F. for the tricosadiynoate ester and at 80° F. or above for the pentacosadiynoate ester. The chromic material can be sensitized to respond to physiologic temperatures (i.e., about 98° F. for humans).

Physiochromic matrices can be formulated to hold the chromic agent in one state until the matrix is dissolved. Once the matrix is dissolved and its effect on holding the chromic agent in one state, the chromic agent is free to change conformation to another state. For example, an acid sensitive, pH reversible physiochromic agent can be dried down with an acid. The acidity can hold the polymer in one colored state. The local concentration of acid is high in the dry state. When a physiologic buffered solution is added, the acid is released and neutralized by the buffer. The physiochromic agent can now covert to an alternative color since it is bathed in a basic environment.

Combination colors can be integrated along with the chromic material to create a variety of color change effects. For example, the brown color used in a variety of food types is made with a combination of yellow, red and blue. The blue food color can be replaced with a blue form of the chromic agent. Upon color change triggering, the brown food color combination can be converted to a bright red-orange. Examples of brown colored foods or beverages include brownie mixes, hot and cold chocolate drinks, cinnamon colors, and the like.

The physical, conformational, or polymerization state change can be used as a mechanism to release or change certain embedded flavors, nutrients, aromatic compounds, nutraceutical agents or the like. For example, a flavor material can be chemically coupled to a monomer non-chromic form compound. In the monomeric form the compound-flavoring expresses a flavor, whereas upon polymerization the monomer becomes polymerized, consequently restricting the flavoring to interact with taste receptors. The restricted form of the flavoring becomes non-flavored. The release mechanism is simultaneously traced with a physiochromic color change as an indicator.

Alternatively, conformational changes in the chromic material matrix can be utilized to release various food grade compounds. For example, polydiacetylene in its blue form is highly ordered on the molecular level. During processing and polymerization, a food grade compound such as a vitamin or flavor can be trapped. Upon temperature or physiochromic triggering of the polydiacetylenic material to the red form, the polydiacetylene becomes disordered and opens at various positions. During the conformational disordering of the polymer, the vitamin or flavor can be released. The monomeric form of the chromic material can be used to absorb and allow in the flavor or aroma. Polymerization could be used to trap in the flavor or aroma. The ordered blue form of the polymer may hold a flavor or aroma where heating results in a conformational change and disorder in the polymer which is useful to release the flavor or aroma.

Specific physiochromic changes may be desirable when developing foods that a producer would like to differentiate from a competitors. Binding moieties can be used to facilitate specific photochromic, thermochromic, or physiochrdmic color transitions. Lectin-receptor agglutinin-receptor, antibody-antigen, biotin-avidin interactions or the like can be used to stimulate a binding pair interaction between different food components. Binding pair interactions can be used to create specific calorimeter changes in the chromic agent. For example, a combination of milk and cereal can be formulated in which a specific type of milk contains one member of a binding pair, such as a multiple biotinylated milk protein and the cereal contains a biologically active form of the physiochromic agent that contains avidin or streptavidin as a second member of the binding pair. When the specific milk comes in contact with the specific cereal, then only that milk will cause the specific cereal to change color through the binding interactions of the binding pair members. No other milk or cereal combinations could cause a chromic change without the selective interactions of those binding pair members. This scenario can help food manufacturers create novel means of brand differentiation.

Carbonation pressure release in opening sealed carbonated beverages may be used to induce a local stress/concentration change, which could cause a color triggering changes in the chromic material. For example, the inside of a liquid container can be coated with a pH or friction sensitive version of the physiochromic material. Upon opening the container and release of built up pressure to ambient conditions, the process of bubble nucleation and local carbonic acid concentration change may be used to cause a change from environmental condition/conformation of the color change agent to another form of the material. If the container is clear, the color change can be made evident to the observer of the color change. The color change agent can either be in a water solution form such as contained within a liposome structure or be coated on the inner wall of the container.

For hydration-activated color change, physiochromic agents which change color depending on the degree of solvation or hydration can be used (hydrochromic agents). Color change agents capable of changing color upon partial or complete hydration and can be ingestible can find multiple uses for food or food related products. For example, the bi-polar diacetylenic compound 4,6-decadiyne-1,10-diol when adhered to a surface and polymerized at room temperature forms a deep blue/purple polymer. The blue/purple polymeric form of the material changes to a red/orange color upon hydration below or above the melting transition of the material. One mechanism for inducing the color change may be rapid intercalation of water between the layers of the crystalline lattice where the aqueous phase disrupts the ordered polymer lattice.

The hydrochromic agent's rate of color change is temperature and configuration dependent. For example, the rate of color change from the blue/purple color to a red/orange color is rapid and occurs within a minute when a thin layer of the hydrochromic agent is uniformly spread over a dry porous structure and exposed to an aqueous fluid at or 10° F. below the melting transition of the material. The color change is slowed significantly from one to several hours if the hydrochromic agent is applied in a thick layer (0.1 to 1.0 mm) and treated with an aqueous solution near freezing.

The hydrochromic agent can be placed on an ancillary material such as carbohydrates, granulated sugar, sugar sprinkles, fondant, sugar pastes, candies, nutritional bits, food coatings, condiments, carriers, emulsifiers, coating materials or the like and subsequently applied to a food surface. For example, the diacetylenic compound 4,6-decadiyne-1,10-diol can be conveniently dissolved in an alcoholic solution (0.15 g/ml) and the solution applied to white or colored sugar sprinkles. Upon coating, drying and polymerization, the sugar sprinkles can subsequently be adhered to a cookie, cereal, candy, bread, cake or the like. The dark blue/purple sprinkle changes to an orange/red color immediately upon treatment with water, milk or other liquids capable of disrupting the crystal packing of the chromic agent.

The use of hydrochromic agent pre-coated sugars, salts or other carriers has the advantage of providing a high degree of coloration and surface area for fluid contact. For example, a fine hydrochromic/sugar particle coating creates capillary channels for fluid to wick through, thereby facilitating the hydration process.

Other structures may also conveniently contain the hydrochromic agent placing it in close or intimate contact with foods. For example, the material can be placed on a bowl, spoon, plate, fork, straws, a hydrating strip, a package insert, part of the package or the like, such that a portion of an absorbent material can be in liquid contact with an ingestible liquid. As the liquid hydrates the structure, the liquid solvent hydrates and migrates along the structure causing the physiochromic agent to change color. If the structure containing the agent is edible, it can remain in contact with the ingestible liquid and be consumed. If the structure containing the agent is safe for contact with food, but inedible, the structure can be removed prior to consumption of the ingestible liquid.

Mechanical/frictional means can be used to induce color changes in a variety of food compatible products. Color changes can be induced using mechanical means primarily including friction due to rubbing, elasticity, and shearing. For visible friction-induced color changes, the color change agent can be permeated into or placed on a surface. Rubbing, stretching, and shearing or other stress-causing action also can be used to induce a frictional force on the color change agent resulting in localized heating. The ease and magnitude of color change is dependent on the transition temperature of the chromic agent, the friction coefficient between the molecules in the composite or a rubbing tool and the thermal insulative/conductive properties of the composite or rubbing tool. Rubbing tools can include a person's fingers, finger nails, teeth, a wooden stick, a plastic implement or the like. Materials that are more thermally insulative may result in more thermal energy remaining with the chromic agent and less being transferred to the composite or rubbing tool. Metal rubbing tools serve as poor devices for inducing a frictional color change, whereas insulative materials such as plastic or wood provide an easier means for inducing a color change.

Mechanical/frictional color change methods are attractive for revealing messages, altering graphics, introducing codes, creating sweepstakes, creating entertaining graphics or the like.

Touching, rubbing mixing, chewing, kneading and various other forms of handling can be used to induce the color change. The color change agent must be responsive to the available amount of frictional forces. The agent must also be stable to ambient temperatures and humidity conditions or a color change may result from influences other than frictional/mechanical forces. An exemplary compound, the blue polymeric form of 10,12-octadecadiynoic acid exhibits good thermal stability up to 100° F. with full hydration, whereas rubbing the dry form of the blue polymer easily triggers the polymer to the red form of the polymer.

Mechanical/frictional triggering can be performed directly on a food surface, on a laminate in contact with the food or on a generic surface. In each case, the triggering process can be used to reveal hidden messages, illuminate branding messages, provide a means of interactive graphical changes or the like.

The mechanochromic material can be applied to a surface by a variety of means including application of a solvent containing the chromic agent by means of ink jet printing, spraying offset printing processes, blotting, pad printing, dipping or soaking. Concentrations of the chromic agent can be from about 2 g/ml to 0.01 g/ml, typically in the range of from about 1 g/ml to 0.05 g/ml, usually from about 0.5 g/ml to 0.1 g/ml. Alternatively, the chromic agent can be applied using transfer methods such as thermal transfer, rubbing from a solid, from a molten liquid or the like.

Photoactivation can be used to cause color changes in foods or food-related products when an appropriate photochromic agent is introduced. Convenience foods containing a photochromic agent when placed in sunlight provide an entertaining means to create a variety of effects. For example, cookies, cereals and various other convenience foods can be used to reveal, various logos, branding identities, codes, sweepstakes information, messages or co-merchandising items to the consumer.

The photochromic agent can be patterned on or applied to the food, packaging material or implement in contact with the food by means disclosed earlier. Photochromic agents have the advantage of not requiring incidental heat of fluids to create a visual effect. Depending on the photochromic agent, the food can either turn from a natural food color to a new hue or from a given hue to an alternate hue.

For thermochromic agents, temperature ranges can include cold temperature for frozen and then thawing (−20° F. to above 32° F.), low temperatures from refrigerator levels to room temperature (33° F. to 60° F.), moderate room temperatures to moderately above room temperature and overlapping temperatures from (61° F. to 100° F.), and room temperature to moderate to high cooking temperatures (70° F. up to 200° F.). The final temperature triggering range for the chromic agent is dictated by the hydrocarbon chain length of the molecule, the intermolecular hydrogen bonding capabilities of the molecule's head group, additional side chains of moieties which influence intermolecular attractions or repulsions or the like, environmental effectors which impact the final temperature triggering transition for the chromic agent, and the degree of polymerization to which the chromic material is exposed. Guidelines can be given, but for a particular transition temperature change, the actual change must be determined experimentally. One can try different amounts of the effectors and graph the effect of the concentration of effectors with the change in transition temperature. A curve is produced which allows the determination of the amount of effector, with the change in transition temperature.

Environmental effectors combined with chromic agent to increase or decrease the thermochromic transition of a given thermochromic agent include: various oils, waxes, low levels of organic solvents such as alcohols, ketones, ethers, chloro- and fluorocarbons, metal ions and other ionic compounds, chelating compounds, emulsifiers, or the like. The effector material can change thermochromic transition by altering the energy required to induce a thermochromic transition in the agent. Oils and organic solvents can interact with the long chain hydrocarbons of a C23 or C25 polydiacetylenic acid. The chain packing can be disrupted by the effector to create a metastable state in the polymer that can, in turn, change color at a lower temperature. For example, the temperature transition can be lowered for a polymerized C25 polydiacetylene polymer in its native dry crystalline state from a temperature range of 150° F.-170° F. (depending on the degree of polymerization) down to 120° F.-130° F. by suspending the crystals in a sugar syrup and adding trace amounts of ethanol. Concentrations of oils or solvents added to a matrix can be from 0.001% to 100%, based on 100% of diyine, more usually from 0.01% to 50%, and typically from 1% to 10%.

The melting transition of the wax or oil in contact with the chromic agent can directly increase or decrease the intrinsic transition temperature of the chromic agent. Oils that solidify under freezing temperatures can stabilize the chromic agent. Upon a temperature increase above melting transition temperature of the oil or wax, the melting process can facilitate the melting of a hydrocarbon side chain on the chromic agent, causing it to undergo a thermochromic transition. The final thermochromic agent triggering temperature can be further adjusted by selecting a specific temperature at which polymerization of the chromic agent is performed. Polymerization at subzero temperatures ($-10°$ F.) lowers the final triggering temperature relative to polymerization at temperatures just above freezing (10° F.). Thermochromic transition temperatures can be increased by increasing intermolecular stability, such as promoting hydrogen bonding of hydrophobic interactions, both between monomeric units within a given thermochromic polymer chain and between the polymer chain and a given effector molecule. For example, the transition triggering temperature of a C23 or C25 polydiacetylenic acid polymer can be increased by embedding the polymer in a high temperature-melting paraffin or wax. The thermochromic material can be embedded in waxes from a concentration of 0.01% to 99%. More usually from 0.1% to 50% and typically from 1% to 10%.

Alternative chromic agent triggering mechanisms and color reporting processes: Alternative triggering mechanisms include the use of enzymes or pre-digestive effectors primarily from saliva which can chemically or biochemically induce a color change in the chromic agent through a catalytic change. For example, enzymes responsible for the initial stages of starch break down occur in saliva. Chromic agents chemically modified with starch or carbohydrate chemistries can be made susceptible to enzymatic activity resulting in a conformational or environmental change which in turn can cause a color change in the chromic agent.

Microbial metabolites, enzymes, or by-products find use as a triggering mechanism for the chromic agent resulting in a means to detect certain bacteria in foods. For example, the chromic agent can be chemically modified to respond to certain by-products produced by *Salmonella*. The chromic agent is placed near or coated on the inner surface of a wrap that is in contact with a processed chicken carcass. If *Salmonella* is present in the carcass and produces a triggering compound the chromic agent is triggered, indicating the presence of *Salmonella*.

An alternative mechanism for microbial detection is the use of a the microbial cell's uptake of monomer forms of the chromic agent. For example, *E. coli* can use diacetylenic fatty acids as a carbon source. Incorporation of the polymerizable acid into a bacterial cell membrane can be detected by ultraviolet irradiation of the bacteria resulting in polymerization of the acid to a blue color. Food processors can simply irradiate food; development of blue color indicates the presence of harmful bacteria.

Importantly, polydiacetylenic materials as a class of intrinsic chromic change agents can be selectively tuned to respond to specific triggering processes relevant to ingestible products. Additionally, polydiacetylenic materials can uniquely undergo multiple different sequential color changes. Examples include photochromic triggering followed by irreversible thermochromic triggering; photochromic triggering followed by reversible thermochromic triggering; photochromic triggering followed by mechanochromic triggering; reversible thermochromic triggering followed by irreversible chemochromic triggering; multiple thermochromic transitions during increasing or decreasing temperature exposure; and other permutations.

Configurations for liquids: Liquid phase monomers can be included in an unpolymerized form in a beverage or consumable fluid, such as in a syrup where the monomer is in a colloidal or microcrystalline state. The monomer can be directly polymerized with an ultraviolet light source or sunlight. The solution suspension monomer can also be pre-polymerized and then added to a liquid phase consumable. The monomer can be made water-soluble using short chain compounds, which are mono- or bi-polar. In this case, the monomer must be prepolymerized in a solid form and then solubilized after polymerization. Polydiacetylenes undergo a topochemical polymerization and must be in a crystalline state in order for polymerization to occur. Monomeric lipophilic forms of diacetylenic compounds can form colloidal particles, such as liposomes, vesicles, or other lamellar forms. Lipophilic forms of the monomer can be crystallized in a colloidal state and polymerized while the monomer is suspended in an aqueous solution. Colloidial or microcrystalline suspensions of monomeric diacetylene can be made using ultrasonication or standard reverse phase vesicle formation methods. Heating and cooling cycles along with intense sonication can be useful for improving uniformity and homogeneity of the suspensions.

For alcoholic beverages, the monomer can be processed into the beverages using reverse phase vesicle formation. The monomer can be dissolved in ethanol and combined with the beverage aqueous constituents. Vesicle formation can be accomplished using standard processes. After the beverage has been formulated, polymerization of the monomer can be accomplished using standard polymerization methods.

Methods for application to foods: Compositions containing either pre-polymerized material or monomer material can be processed into foods using a variety of application methods such as ink jet printing, pad printing, extrusion, spraying, liquid applicators, dip coating, sublimation, spreading, application of laminates containing the material such as sugar layers or rice paper, edible labels, dripping, dye sublimation printing or the like. The method of interest will depend on the food substrate utilized, the composition to be applied and the desired format in which the composition is to be placed.

Coating Matrices and coating methods for sugars, salts, shredded and powdered cheese, flower, grains, nonpareils, and other powdered forms of foods. Polyethylene glycol coating matrices for cereals and cookies are practical due to the unique solubility properties of polyethylene glycol polymers.

Co-coating matrices can have the combine properties of helping to adhere the chromic agent to a food type, suspending the chromic agent in a matrix to maximize the visual appearance of the chromic agent, helping to modulate the activity and performance of the chromic agent, helping to minimize the amount of chromic agent required, and the like. For example, the coating matrix can have the property of allowing the chromic agent to undergo a conformational transition from one color to another by providing the necessary flexibility required by the chromic agent.

The coating matrix can also provide a source of inducing defect structures in the solid phase of the chromic agent or as a means for introducing doping agents along with the chromic agent as enhancers to improve the agent's optical performance. Doping agents can be used to enhance the optical properties of irreversible and reversible chromic agent changes. Low levels of additives can be used to enhance the colorimetric changes that the material can undergo. Doping materials can include chemically/structurally related compounds which help create a molecular environment favorable to the transitions necessary for the chromic agent to undergo changes during its transition from one color to another.

The coating matrix can also help provide a protective barrier for the chromic agent by minimizing the unwanted effects due to oxidation, moisture, or stabilization of the chromic agent of effectors of the chromic agent during storage and shipment of the final end product to the consumer or during product production.

Coating matrix solutions can be made using a variety of solvents including polar protic solvents such as water ethanol and methanol, apolar organic solvents such as dichloromethane, polar aprotic solvents such as acetone, or the like. It is desirable to use solvents that are considered food grade such as non-denatured ethanol.

For application to cereals, it is desirable to place the photochromic, thermochromic, or physiochromic material in a carrier material such as a sugar matrix whereby the matrix is applied as a coating to the cereal during production. For application to convenience foods such as flat pastries or cookies where patterning is important, high-speed printing techniques are important. In this case it is desirable to use a soluble form of the material so that it can be incorporated directly into the liquid matrix used for printing.

The monomer or polymeric material can be applied to a solid food using a laminate overlay where the base material in the overlay/laminate is itself edible and contains the monomeric or polymeric color change material. Rice paper can be used as a laminating material which when wetted and containing the polymer can be easily adhered to the food as a substrate. Laminates can contain the chromic agent in combination with sugars, carbohydrates, digestible polysugars, or proteins, which give the laminate a stable layer. The layer can have the property of being directly layered on to a food surface, fused and then activated for photochromic, thermochromic or physiochromic activity. Food laminates capable of containing the chromic material can be any commercially available product or formulation that is physiologically acceptable and can be printed or coated. For example, the laminate can be a marzipan sheet available through most bakery supply sources. The thin sheet can be printed, stamped, blotted with the chromic material by any convenient means, dried and polymerized. The laminate can then be adhered to the food type surface alone or with food pastes.

Commercially-available laminate/paper materials compatible with ink jet printing can be used (Kopykake, Torrance, Calif.). Commercially-available ink jets can be modified to contain an ink version of the chromic agent. The ink jet cartridge can be used with an aqueous or solvent-based solution containing the chromic agent. The food grade laminate/paper can be inserted into the ink jet printer and standard ink graphics printing programs utilized to generate text and graphics. The laminate approach provides a means for generating high-resolution graphics and text and transferring the images or text directly to the food type. The laminate can be made to be compatible with the food flavor and texture. For example, it is desirable to have a sugar-based laminate for sweet products such as pastries, cookies, and certain convenience foods. Alternatively, it is desirable to have a salt/seasoning-flavored laminate for dairy or processed meat products. The exact composition, flavor, and texture of the laminate will depend on the food component into which the chromic material is integrated. Laminates have the advantage of being separately prepared from the food product and then processed to be a part of the food. Parallel processing provides for high-speed production and simplified implementation.

Edible food grade labels, paper or wrappers containing the chromic material can be used for a wide range of general applications. The label can be made with a digestible carbohydrate material rather than a non-digestible cellulosic material. Printing the chromic material can be accomplished by standard printing means. The printed chromic label can be applied to any solid and reasonably flat surface such as a cookie, a toaster pastry, baked goods, and a variety of convenience foods. A major advantage to chromic labels is that they can be pre-mass produced and subsequently applied to finished foods rather than requiring changes in existing food production processes. The chromic material can made soluble in ethanol or various highly volatile solvents, which can be quickly evaporated, or in an aqueous solution, which can be absorbed. In any case, it is desirable to coat the surface of the food substrate with the chromic material so that upon polymerization the chromic material is highly visible. The substrate can be dipped into a solution containing the chromic agent, thereby coating the agent on the substrate's surface.

Entertainment foods such as marshmallows can incorporate the chromic material using dip coating or spraying processes to provide an extra level of enjoyment, especially for children. Chromic marshmallows can be produced to respond to ambient temperatures such as touch or elevated temperature fluids, like hot chocolate. Marshmallows can be directly dip coated with a higher temperature thermochromic material dissolved in an alcoholic solution. After drying and polymerization to produce the dark colored chromic agent, the marshmallows would remain dark until exposure to high temperatures such as an open flame. Upon exposure to any elevated temperature, the dark marshmallow would turn bright orange-red.

Alternative means of incorporating the chromic agent into foods could include biochemical substitution. Fruits, vegetables, certain meats, bacterial cultured dairy products such as yogurt, grains, rice, beans or other amenable foods can be grown with the precursor monomeric material as a nutrient for the growing food. Upon incorporation or biochemical uptake of the precursor monomer through the appropriate pathway into the food product, the food can be irradiated with ultraviolet (254 nm) to cause polymerization of the foodstuff. Various dairy products such as cheeses, milks, and yogurts that naturally contain bacterial cultures to aid in digestion can be made with monomeric and/or polymeric chromic agents.

Spectral colors relating to chromic change agents: The color, contrast, and hue can be adjusted to give a chromic change agent particular visual characteristics. Color change characteristics can be achieved by changes in the chromic agent itself or in combination with stationary-base colors associated with the same matrix as the chromic change agent. Various permutations of base colors in combination with the initial color of the chromic change agent will give one visual color to start with and often an unexpected color with which to finish. Chromic change agents with chromically reversible properties can be used to achieve repetitive visual effects compared to irreversible chromic change agents that can be used to achieve a one time effect.

Standard Pantone Colors, RGB, CMYK and colors typically used in the food industry can be used in combination with the chromic change agent. Examples of color change options based on the change of the chromic agent alone (white or clear base color) or in combination with a other base colors listed below but are not limited to any specific example are shown in Table 1.

In addition, color additives such metallic flakes, glitters, sparkles, and other elements which augment colors, can be used to create desirable visual effects. For example, silver coated non-pareils can be coated with a red reversible form of the chromic change agent to give the effect of a shiny red anodized sphere. When the combination is cooled, the coated non-peril appears to have a dark blue metallic anodized coating.

TABLE 1

Color change options based on initial chromic color and base color.

| Initial Chromic Color | Base Color | Starting Combination | Triggered Color |
| --- | --- | --- | --- |
| light blue | white/clear | light blue | pink |
| medium blue | white/clear | medium blue | orange |
| dark blue | white/clear | dark blue | red/orange |
| magenta | white/clear | magenta | red |
| magenta | white/clear | magenta | blue |
| red | white/clear | red | blue |
| red | white/clear | red | yellow |
| yellow | white/clear | yellow | red |
| blue | yellow | green | orange |
| pink | yellow | magenta | green |
| red | yellow | orange | brown |
| orange | orange | dark orange | dark brown |
| orange | light blue | purple | dark blue |
| orange | light green | red/green | gray green |
| orange | pink | red | purple |
| red | tan | deep red | blue/purple |
| light blue | light green | gray green | red/green |
| yellow | red | orange | red |
| yellow | light tan | golden | brown |
| red | light blue | brown | orange |
| red | light green | brown | navy blue |

Food grade metallic and pastel colorants (Linton Paper & Supply, Inc.) can also be used in combination with the chromic change agent to give a sparkle-like effect. More granular colorants can be used to give a matte-like finish to the coating.

Methods for polymerization: Polymerization can be accomplished either prior to processing with the food or after the monomer has been processed with the food. The photochromic properties of the chromic material can be used to create patterns and messages on the surface of solid foods. Increasing or decreasing the level of polymerization of the chromic material is used to increase or decrease, respectively, the temperature or other means of inducing color changes in the polymer:food matrix or the like used to trigger a chromic change in the material. For example, different zones of a food surface, which contains the chromic material, can be polymerized to different levels. Each zone can, depending on the level of polymerization exposure, change color sequentially as the temperature rises. The chromic change zones can tell consumers that cooking is in progress but not yet done. As cooking continues and as the last zone changes color, the consumer can ascertain that cooking is complete.

Zones which change colors at increasing temperature can be used for food safety purposes indicating to preparers or consumers when the food is cooked to a temperature level and any contaminating bacteria have been killed (e.g., 160° F.). Zones would be calibrated to accommodate higher external temperatures during cooking.

Increasing or decreasing the localized concentration of chromic material in combination with controlling the local level of polymerization can be used to create complex patterns on the surface of a food type. Increasing the local concentration in one area relative to another area will create a higher relative triggering temperature in the high concentration zone relative to the lower concentration zone. The patterns can be developed to create the visual appearance of a changing graphic throughout the temperature triggering process.

In addition, standard food colors can be used in combination with the chromic material to create full color designs and patterns. The visual representation of a graphic that changes color and apparent pattern throughout the heating process can have significant value in that it can be used for commercial, promotional, merchandising and advertisement purposes. In some cases, polymerization can be accomplished by the consumer where, by opening a package and placing the foodstuff in sunlight, a color begins to appear immediately prior to consumption. For example, drinks or cookies can be made to change color in the sun. In other product formats, the photochromic food may be purchased along with an appliance or hand held ultraviolet lamp which can be use to expose the photochromic material.

Thermal polymerization can be utilized in certain foods. Thermal polymerization provides for photochromic color development of the chromic agent without the need for an external ultraviolet light source. Certain forms of diacetylenic compounds that are highly ordered, yet provide flexibility for reorganization, can self-initiate polymerization under mild conditions. For example, the crystalline form of the methylester of 10,12-tricosadiynoic acid will polymerize in the dark and in absence of ultraviolet light. The thermal polymerization temperature may be substantially different from the thermal color change transition temperature. Polymerization may occur at a lower temperature, e.g. 10-20° F., than the thermal transition temperature.

Patterns in the chromic agent can be generated by selectively placing the agent in locations using methods such as ink jet, pad, extrusion or offset printing followed by polymerization of the chromic agent. Alternatively, the patterns can be generated using a continuous evenly coated area of the chromic agent followed by photo-masking techniques. Ultraviolet light-transmitting photomasks can be utilized. In either case, high-resolution graphics and line art can be generated directly on the food surface.

Ingestible chromic change particles dispersed throughout ground meats as an intrinsic internal thermometer: The United States Department of Agriculture now recommends not using the color of cooked ground meats to determine doneness and whether or not that the meat has been cooked to a safe level (greater than 160° F.). The chromic change agent can find use as an element dispersed throughout ground meat that turns color only when the center of the ground meat has reached an internal temperature of 160° F. The chromic agent can be coated on any compatible food grade additive that can be admixed with the ground meat prior to cooking. The chromic change agent/additive can be introduced into the ground meat at the meat processor level or by the consumer immediately prior to cooking. Chromic change agent particles can be dispersed into ground meats at a concentration that allows the particles to be visualized any time the meat is exposed when cut open. The chromic change agent particles can be dispersed at a concentration of one per centimeter cubed to a concentration of 1000 per centimeter cubed. More often the chromic change agent particles can be dispersed at a concentration of 10 per centimeter cubed to 500 per centimeter cubed. Usually, the chromic change agent particles should be present from a concentration of 25 per centimeter cubed to a concentration of 100 per centimeter cubed. Chromic change agent particles obviate the need for thermometers since the meat itself can posses the temperature sensing capability. The cook or consumer need only cut into a piece of meat during cooking to determine accurately the internal level of doneness of the meat being cooked.

Ingestible chromic change particles integrated into foods may find broad use in cooking or warming other items as well. For example, they can be used for baked goods, in food service for monitoring holding temperatures, processed, pre-cooked meats such as hot dogs, in food processing, in microwaveable foods, and various other related products or processing.

The chromic change agent can be conveniently coated onto a particle such as a spice, sesame seed, oatmeal flake, protein particle, soy based particle, carbohydrate particle or any other food compatible matrix particle that is of size which can be identified by eye. The chromic change agent can be coated as a film on the surface of the particle to give the particle a characteristic color that is differentiated from the ground meat with which it is admixed.

Chromic change agent particles can range in size and shape. Typically the chromic change agent can be a sphere, a disc, egg shaped, a flake, a random globule, a ring, various geometric shapes, a rod or noodle shape, or the like. The chromic change agent particle can be as small as a 0.5 millimeters along its longest axis so as to be visible by eye to as long as sever centimeters. More usually the chromic change agent will one to 10 millimeters along its longest dimension and typically 2-5 millimeters in length.

Chromic transition conformational change as a depot release substance: The chromic transition may be used as a releasing mechanism for nutrients, vitamins, ingestibles, drugs or the like base on the structural change that it can undergo when it is triggered from one color to another. For example, polydiacetylenic material is known to undergo a significant conformational change during its transition from one color to another. The blue form of the polymer is well ordered system comprised of parallel strands of extended and conjugated double and triple bond units. Side chains and substituents are ordered along with the polymer backbone in a lattice structure. When the ordered macromolecular structure is chromically triggered, it becomes disordered and an open lattice. The chromic change mechanism can be used as a means to release a substance embedded within the lattice matrix. Opening the matrix can be used to release the embedded constituents. The chromic process has a dual function: first, it can act as a releasing mechanism and second, it serves as a color change indicator as to when the release occurs.

Wording or graphics printed on the side of over-the-counter or prescription drugs can be printed with a low temperature irreversible thermochromic material, indicating to the consumer, pharmacist or medical specialist that the drug has been stored at a safe temperature or has been spoiled at a higher temperature.

A chromic change agent may be incorporated into throat lozenges to tell the consumer that they have an elevated body temperature or fever. Alternatively, an aqueous form of the chromic material can be added to a mouthwash, spray or gargle that changes color if the user has a fever.

Alternative thermochromic materials: Alternative thermochromic materials that may have application as ingestibles include leucodyes, transition melting waxes, pigments that are released during hydration or shear, micro and nano-pigments, molybdenum, doped or undoped vanadium dioxide, mercuric iodide, indolinospirochromenes, spiropyrans, polythiophenes, polybi-thiophenes, di-b-napthospiropyrans or the like. Alternative chromic change agents can be combined with food matrices using methods described earlier. Methods for the preparation of spiropyrans, including (Keum et al. (1995), *Bull Korean Chem Soc* 16: 1007), polythiophenes (Lévesque et al. (1996) *Chem Materials* 8: 2843) and various other chromic change agents (Brown et al., eds., (1972) *Photochromism, in Techniques of Chemistry*, Vol. 3; Durr et al., eds., (1990) *Photochromism: Molecules and Systems* (*Studies in Organic Chemistry*, 40)) have been described. All of these above references are incorporated herein by reference. Extensive modification or encapsulation may be required with compounds such as these to ensure safe ingestion and consumption without toxic side effects.

Compounds such as spiropyrans and the like are of interest where the thermochromic change agent exhibits a color at one temperature and disappears when the temperature is altered. Spiropyrans, polydiacetylenes and other related materials that change color or become transparent can be used to reveal messages or graphics when overcoated on a permanent pigment. Making messages appear or disappear is of interest to the food and entertainment industries for promotional, marketing, and sales programs.

Combinations of different chromic change agents: In some cases, multiple color changes may be desirable or required on some products. Different chromic change agents or classes of agents that change color in response to different triggering mechanisms may be used on a single product as distinct pH indicators, time temperature indicators, dissolved gas color indicators, ionic strength indicators, moisture indicating materials, chemical color change indicators, various photochromic materials, various thermochromic materials, various mechanochromic materials, or the like. Combinations of polydiacetylenes, indolinospirochromenes, spiropyrans, polybithiophenes, leucodyes, di-β-napthospiropyrans, and other intrinsic color change agents, can be used alone or in combination. Combinations of these chromic change agents can be accomplished by either co-mixing different agents homogeneously or selectively placing the different chromic agents in zones so that each agent can be triggered by its designated triggering method.

A variety of optical effects and applications can be envisioned by using multiple chromic change agents either specifically patterned or coprocessed. For example, a series of chromic change agents can be patterned by a dot matrix or offset printing process such that the zones or images of one type of chromic agent can be visualized at ambient temperatures or conditions. When the ambient temperatures or conditions are altered, such as processes including cooking, heating, food preparation, eating or digestion, the patterns change in response to particular triggering mechanisms. The chromic change patterns can be specified or preprogrammed to achieve particular memory effects that can be entertaining and/or informative. Entertaining pattern changes find use in promotional applications such as a color change process that leads the consumer stepwise through food purchasing, preparation and consumption. Multipart color images or patterns and/or conditions which change in a complex or intricate manner may necessitate the use of multiple chromic change agents. Patterns that appear on ingestibles due to the response of chromic change agents include text, characters, images, symbols, branding identities, messages, icons, logos, artistic designs or decorative designs.

Complex color patterns comprising multiple chromic change agents may be used to communicate directions or recipes to a potential or actual consumer. By way of example, a prepackaged food item may incorporate a message on the item that suggests that the item be purchased. After the package is opened, exposure to air, light or room temperature may cause the disappearance of the first message and a second message such as "Now add substance A" to be displayed. Addition of substance A may induce a chemical change that leads to a chromic agent-induced pattern change and the next message, which may state, for example, "Now bake at 350° F.", "Add substance B", or the like. In addition to text-based messages, an ingestible may be imprinted with a series of graphical or "universal" displays that direct the consumer to the next step. Examples of ingestibles that communicate directions may include food items, pharmaceuticals or pills, or disposable swabs or other devices that require some degree of preparation by the preparer or consumer.

Complex information pattern changes also find use in diagnostics and sensing applications where the pattern change results when an ingestible is consumed, digested and excreted, as described below.

Chromic change agents as diagnostic indicators: Intrinsic color change agents that are irreversible in color change can be used when it is important to preserve permanently or record a physiological process. Intrinsic color change agents that are reversible in color change can be used when it is important to record repeatedly a physiological event and/or be able to trigger reversibly a chromic change agent to confirm how it was originally recorded as a diagnostic mechanism.

The chromic change and substance release system can find use in various ingestibles where it is desirable to indicate to an individual or health care worker that a drug, nutrient, over-the-counter medicine or the like has been appropriately released into the individual's digestive system. For example, a chewing gum or similar product that is retained in the mouth rather than swallowed, and that contains a chromic change agent combined with a drug for delivery by chewing, can change color due the sheering forces of chewing or from reaction with salivary chemicals or enzymes. The chromic transition and corresponding color change serves as an indicator to the individual that the substance has been fully released from the gum and that further chewing is no longer necessary in order to obtain the full effect of the substance.

A chromic change agent may be incorporated on an diagnostic ingestible, such as a throat lozenge, which indicates the presence of a pathogenic microorganism. *Streptococcus pyogenes*, the causative agent of streptococcal sore throat, is one such microorganism that may be detected by this means. A chromic change agent may be associated with one of a binding pair such as an antibody, enzyme substrate, receptor ligand, etc., that interacts directly or indirectly with the microorganism or its products. For example, a chromic change agent may be incorporated in the lozenge in a liposome or other lipid-based composition that is modified by a lecithinase from the bacterium. A chromic change agent that interacts when it contacts salivary components or other bacterial metabolic processes or products could then change color upon release from the liposome. Alternatively, a chromic change agent may be linked to one of a binding pair, and interaction with the other binding pair member causes a chemical change in the environment of the chromic change agent and a subsequent color change. An example would be a chromic change agent bound to an enzyme substrate, wherein the substrate is specific for a particular microbial enzyme. The substrate alters the pH or redox potential in the environment of the chromic agent when acted upon by the microbial enzyme, inducing a color change as a result of a change in, for example, the ionization or redox potential of the chromic agent.

A diagnostic color change ingestible can be used by the medical community to evaluate a number of digestive tract disorders or bodily dysfunctions in vivo. Devices can be constructed with color change agents in selective patterns alone or in combination where they are placed on a carrier such as a pill-sized bead or the like, and then consumed. As the carrier is ingested and travels through the digestive tract, it encounters various points at which it can be triggered, and its color changes in a particular color-changing zone. As the digestive process continues, the carrier can record the wellness or dysfunctional state of the digestive process. As the carrier is excreted during a bowel movement it has a record of information of the digestive process and can be used to give the consumer or physician general or specific information about the digestive functionality in vivo. In order to facilitate recovery and separation of the diagnostic color change ingestible from fecal matter, a separation means can be incorporated into the ingestible, such as, for example, a magnetic core.

Ingestibles incorporating chromic change agents may also find use as a detection method for bodily dysfunction such as ketosis or liver dysfunction resulting in the lack of ability to properly metabolize certain food components. The resulting biochemical by-product in breath or saliva can act as a trigger for a color change in the chromic agent, the change indicating the presence of a bodily dysfunction. The chromic change agent can be incorporated into a mouth wash, a gargle, a spray, or other convenient form that enables saliva or breath to come in contact with the chromic change agent and trigger a color change as an indication of a dysfunction.

EXAMPLES

Specific foods or other compositions that are taken orally that have been or can be used with the subject invention, as illustrative of ingestibles generally.
Kellogg's Pop-tarts
Nabisco Cream of Wheat
Marshmallows
Kellogg's Rice Crispy Treats
Easy Bake Oven Products
Karo Syrup Kellogg's Fruit Loops
Kraft Foods Jell-O
Hormel Franks Bologna
Pepperidge Farm Goldfish Soup Crackers
Nabisco Newtons
Flintstone Vitamins
Tums Antacid
Crest Toothpaste
Listerine Mouthwash
Throat lozenges
French toast sticks Burger King Cinnamon Buns Pillsbury frosting
Cinnamon Minis—Special dip frosting—Burger King Example 1

Synthesis of Chromic Agents

Synthesis of N-ethanol-hexadeca-5,7-diyneamide: 1 molar equivalent 5,7-hexadecadiynoic acid (GFS Chemicals) was dissolved in dichloromethane to a concentration of 100 mg/ml and stirred at room temperature. 1.05 equivalents of 1,1-dicyclohexyl carbodiimide (DCC) were added and the mixture stirred. An immediate white crystalline precipitate formed indicating the presence of dicyclohexyl urea (DCU). The reaction mixture was stirred for 1 hour at room temperature. Ethanolamine (99.5% pure, Aldrich Chemicals) was added drop wise to the unfiltered stirring solution. The amide formation was checked periodically using TLC and spotting a filter paper then ultraviolet 254 polymerization and testing reversible thermochromism (85° F. red/60° F. blue). The reaction was complete within 1 hour and left standing for a total of 4 hours at room temperature. The DCU was filtered from the reaction mixture using gravity filtration (Whatman 541) and allowed to stand at 4° F. over night. Additional DCU crystals formed over night and were filtered using gravity filtration (Whatman 541). The solvent and residual ethanolamine was remove using a Rotovap. The reaction product was resuspended in dichloromethane and refiltered using gravity filtration (Whatman 541). The solvent was removed a second time using a Rotovap. The reaction product was suspended in hexane/dichloromethane solution (20/1 volume/volume). The suspension was warmed to near the boiling point of the solvent mixture to dissolve the product. The reaction crystallization mixture was kept at room temperature for 6 hours. The crystallized product was filtered using gravity filtration (Whatman 541), redissolved and recrystallized a second time.

N-ethanol-hexadeca-5,7-diyneamide can also be prepared by an alternate synthetic route whereby the 5,7-Hexadecadlynoic acid can be converted to an acid chloride and added directly to a stirring solution containing ethanolamine to yield the final amide product. This route has the advantage of more direct purification since it eliminates the need to remove a coupling agent such as residual DCC or the DCU byproduct.

Synthesis of methyl 10,12-pentaeosadiynoate (MePDA): 10,12-pentacosadiynoic acid (10 gm., GFS Chemicals) was dissolved in a solution containing 10 ml methanol (HPLC grade) and 10 ml chloroform (HPLC grade). The solution was stirred at room temperature and 10 drops of neat sulfuric acid was added drop wise. The solution was warmed to 100° F. for 2 hour. The reaction mixture was purified using column chromatography. The product (MePDA) was dried using a Rotovap and the material stored in a chloroform solution. The solid form of MePDA was very unstable to polymerization and therefore kept dissolved in organic solutions.

Synthesis of methyl 10,12-tricosadiynoate (MeTDA): 10,12-tricosadiynoic acid (10 gm., GFS Chemicals) was dissolved in a solution containing 10 ml methanol (HPLC grade) and 10 ml chloroform (HPLC grade). The solution was stirred at room temperature and 10 drops of neat sulfuric acid was added drop wise. The solution was warmed to 100° F. for 2 hour. The reaction mixture was purified using column chromatography. The product (MeTDA) was dried using a Rotovap and the material stored in a chloroform solution. The solid form of MeTDA was very unstable to polymerization and therefore kept dissolved in organic solutions. Alcoholic solutions of MePDA and MeTDA: Solids MePDA or MeTDA were dissolved in reagent grade ethanol to a concentration of 150 mg/ml. A residual polymer was removed by filtration through Whatman No. 1 filter paper. The solutions were held at room temperature or slightly above (70-75° F.) to avoid crystallization or precipitation.

Synthesis of dimethyl bis(10,12-pentacosadiynyl oxyethyl) ammonium chloride (BRONCO): 10,12-Pentacosadiynoic acid (5 gm. 13.4 mmol., GFS Chemicals) was dissolved in 60 ml dichloromethane and filtered (Whatman No. 1) resulting in a colorless solution. 1,3-Dicyclohexylcarbodiimide (3.6 gm, 17.5 mmol., Aldrich Chemical Corp.) and the base 4-dimethylaminopyridine (one equivalent, Aldrich Chemical Corp.) were added to the solution and stirred for 15-20 minutes during which time a white crystalline precipitate, dicyclohexylurea, formed. Bis(2-hydroxyethyl)dimethylammonium chloride (1.14 gm., 6.68 mmol., Acros Organics-Fisher Scientific) was added to the reaction mixture and stirred over night in a dry inert atmosphere (nitrogen). The urea precipitate was filtered out using (Whatman No. 1) and the reaction mixture was purified using column chromatography. Dimethyl bis(10,12-pentacosadiynyl oxyethyl)ammonium chloride, Bronco, was dried using Rotovap and stored in a powder form.

Alcoholic Monomer Solution of TDA/PDA: 10,12-Tricosadiynoic acid (TDA, 6 gm GFS Chemicals) and 10,12-pentacosadiynoic acid (PDA, 0.9 gm GFS Chemicals) were dissolved in 60 ml ethanol (Fisher). The solution was slightly warmed and stirred. The solution (TDA/PDA) was filtered (Whatman No. 1) to remove residual polymer. Dye colorant could be added to the alcoholic monomer solution as an indicator. Standard organic solvent based dyes were added at 2 drops per ml.

Example 2

Preparation of Edible Printed Laminates

Ink Jet Printing: Black ink jet cartridges (Hewlett Packard 680C compatible or Cannon BJC2000) were modified to contain either the TDA/PDA or MePDA alcoholic monomer solutions. The cartridges were opened and the water based ink removed. The cartridges were flushed with ethanol and the alcoholic monomer solutions added separately to each cartridge. The cartridges were sealed, purged, and inserted into an ink jet printer (Hewlett Packard 680C or Canon BJC2000). Standard word processing and graphics programs were utilized for printing. The ink jet cartridges were cleaned periodically to remove residual build up of monomer caused by drying.

Ink Jet Printed Thermoceromic Sugar Laminates: Edible laminates for ink jet printing (Kopykake, Torrance, Calif.) were printed using the TDA/PDA or MePDA monomer solutions, food grade ink jet dyes, and the ink jet printing systems described above.

Air Brush Coating Surfaces: Alcoholic solutions contain TDA, PDA, TDA/PDA mixtures, or MePDA or an aqueous solution containing BRONCO were prepared according to the methods described above and sprayed onto food surface using a standard hand held air brush Badger model 200, USA). Solutions were thinned or concentrated with their corresponding solvent to achieve desired coating. Coating was accomplished by applying a steady stream of vaporized material to the surface at a distance of 1-6 inches. Patterns were formed using paper stencils or by careful hand movement. After coatings were applied and allowed to dry, the surfaces were polymerized using a hand held ultraviolet lamp (254 nm).

Example 3

Temperature Triggered Chromic Change Agents

1. Temperature Indicating Ingestibles 130-150° F. Thermochromic Corn Syrup: Temperature indicating syrup for hot pancakes, waffles, or the like were made using a microcrystalline suspension of a polymeric polydiacetylene. 2 gm 10,12-tricosadiynoic acid was mixed with 45 ml corn syrup (Karo brand Best Foods, Englewood Cliffs, N.J.) and then probe sonicated at 40% power using a 400 watt sonicator (Cole Parmer Instruments, Vernon Hills, Ill.) for 5 minutes. The sample heated to about 140° F. during sonication. After uniform mixing, the sample was allowed to cool to room temperature (3 hours). A white cloudy suspension appeared within 1 hour. The sample was mixed using a stir rod until a creamy consistency resulted. The sample was polymerized to a deep dark blue color in a shallow plastic container using a hand held ultraviolet lamp (254 nm, Cole Parmer Instruments, Vernon Hills, Ill.). The sample was irradiated for 4 minutes and mixed using a stir rod.

The dark blue syrup was immediately available for use with hot foods. The syrup could easily be spread on hot toast or waffles. Upon application to the food, the dark blue syrup turned bright red in color indicating the surface temperature of the hot food it was applied to. The thermochromic transition temperature occurred at between 130° F. to 150° F.

110-130° F. Thermochromic Corn Syrup: Moderate temperature triggering corn syrup was made using the formulation described above and by adding absolute ethanol at 5% by volume. The ethanol was added to a premixed unpolymerized suspension. The suspension and ethanol were mixed to uniformity for 5 minutes at room temperature and polymerized using the identical conditions described above. The thermochromic transition temperature of the polymerized mixture occurred at between 110° F. to 130° F.

Temperature Indicating Thermochromic Icing/Syrup: 5 ml of the MePDA alcohol solution (above) and 10 gm cake icing (Signature Brands, LLC, Ocala, Fla.) were uniformly mixed at room temperature for 10 minutes. Most of the ethanol from the solution evaporated. The resulting creamy paste was chilled to below freezing (−10° F.) and then exposed to an ultraviolet lamp (hand held, 254 nm) for 5-10 minutes while remaining chilled. The mixture was churned during exposure to give a uniform blue appearance. The thermochromic icing was temperature triggered by simply raising it above freezing (greater than 50° F.). The icing immediately turned bright red when applied to surfaces exposed to room temperature, directly exposed to room temperature, or touched by directly by hand. Oils contained within the icing helped to facilitate the temperature triggering of the thermochromic agent in the icing. Partially hydrogenated vegetable oils (soybean and cottonseed) are solid in nature at freezing temperatures, keeping the blue polymeric MePDA stable. As the oils melt at above room temperature, the polymeric MePDA is subsequently influenced to transition from a dark blue color to a bright red. The icing was further packaged in air sealed plastic pouches (4 mil, polyethylene) and heat-sealed using a conventional heat sealer. Care was taken not to expose or contact the dark blue frosting to temperatures above freezing. The frosting/syrup could conveniently be extruded onto a pastry surface. During the application, the dark blue color turned immediately bright red due to finger contact with the pouch and exposure to a room temperature surface.

Low Temperature Indicating Marshmallows: Marshmallows were quickly dip coated into the MePDA alcohol solution and allowed to dry at room temperature or below. The monomer dip coated marshmallows were exposed to ultraviolet light (hand held lamp, 254 nm) and rotated for uniform polymerization (approximately 2 minutes) until they became dark blue. The marshmallows were stable at room temperature or below (68° F.). They immediately changed to a bright red/orange color upon direct touching, contact with warm fluids, or placing in the presence of an open flame (95° F. or above).

High Temperature-indicating Hot Chocolate: Yellow dye number 6, red dye number 40, and a medium blue polydiacetylenic thermochromic agent that turns orange when triggered by heating were added to a hot chocolate mix prepared at room temperature. The resulting combination of hot chocolate, dyes and thermochromic agent was brown in color. When hot water was added to the solution, the brown color changed to a combination of yellow and red, bringing the brown mix to a bright orange color.

2. Cooking State-Indicating Ingestibles

Temperature Indicating Frozen Waffles: Frozen waffles (Eggo brand, Kellogg Company) were removed from their package and immediately sprayed with an alcohol based monomer solution (above). Waffles were coated at 68° F. using a standard airbrush. Patterns were created using the square cells on each waffle. The monomer solution dried immediately on the waffle surface. The monomer-coated waffles were polymerized using a hand held ultraviolet lamp (254 nm, 6 inches for 10 to 60 seconds). Radial polymerization gradients were used to increase the level of polymerization from the outer region of the waffle to the center. Increasing the level of polymerization causes a corresponding increase in the final colorimetric temperature transition of the thermochromic agent. The resulting waffles had a dark blue appearance upon polymerization. The patterned thermochromic indicating waffles were conveniently re-stored in the freezer prior to use. The temperature indicating waffles were toasted using normal instructions on the package. As the waffles were heated, the dark blue color changed to a bright red/orange. The outer portions of dark blue changed color first. As heating continued, the inner portions of blue at the center of the waffles turned color to red/orange last. The color transition was complete when the waffles were fully heated indicating that toasting was complete and the waffles ready to serve.

Ground meat patty possessing a chromic change agent particle for indicating internal safe cooking temperatures: Chromic change particles were prepared by coating sesame seeds with a thin layer of a chromic change agent. An ethanol solution was prepared with ethanol (Spectrum Chemicals, Inc.) containing 150 mg/ml 10,12-tricosadiynoic acid and 15 mg/ml 10,12 pentacosadiynoic acid. The solution was warmed to 100° F. to dissolve all of the diacetylenic acid. 10 gm sesame seeds were placed in a screw cap vial and saturated with 2 ml of ethanolic solution. The seeds and solution were shaken and tumbled for 3 minutes to ensure complete coverage of each seed. The seeds were poured into a Teflon coated dish and tumbled for 10 minutes with a gentle air stream to ensure that all of the ethanol solution was removed. The coated particles were vigorously shaken and exposed to ultraviolet light (hand held lamp, Cole Parmer, Inc. 254 nm) for 5 minutes resulting in the deep blue appearance of the polydiacetylenic polymer. The coated particles were stored overnight at room temperature.

The blue polymer coated particles were admixed with ground hamburger meat to a concentration where multiple particles were present in the central region of a patty each time a patty was sliced through Patties was grilled on a gas grill and flipped over during cooking. The center of patties were systematically tested during grilling to determine the extent of color change during cooking. Color change particles toward the outer segments of a patty turned color to a bright red/orange earliest during cooking. Color change particles in the center of a burger turned color to a bright red/orange once the burger's internal temperature achieved 160° F. indicating that the burger was cooked thoroughly.

Baby Food: The likelihood that a child will be burned by ingesting overly-heated baby food solids and liquids may be significantly reduced by using a color reversible thermochromic agent combined with a food or formula. Solid foods or formulae may be prepared with a blue thermochromic agent. Upon heating the food or formula the thermochromic agent changes color to orange, indicating a high temperature, which then reverts to the blue color when the temperature of the food or formula is safe to ingest. The thermochromic agent can also be used to indicate uneven temperature distribution in various regions of the food or formula, and that the food should be mixed to achieve a more uniform, safe temperature.

Thermochromic Graphically Patterned PopTarts: PopTarts (Kellogg Company) were coated with a commercially-available sugar glaze and allowed to dry for several hours at room temperature. Edible laminates jet printed (Kopykake, Torrance, Calif.) with either TDA/PDA or MePDA monomer solutions and the Kopyjet ink jet printing system as described above were applied to the glazed PopTart surface. Initially the glaze surfaces were slightly wetted to facilitate the adherence of the edible laminate. Various entertaining patterns were graphically rendered for application on the PopTarts. The monomer printed surfaces were polymerized using a band held ultraviolet lamp (254 nm) at a distance of 3 inches for 5 to 10 seconds depending on the desired level of blue color. TDA/PDA printed/polymerized PopTarts changed color from a dark blue to a bright red/orange when exposed to toaster or microwave temperatures. MePDA printed/polymerized PopTarts changed color from a dark blue to a bright red/orange when exposed to finger touch or above 90° F.

Franks and Hot Dogs: Processed hot dogs can be impregnated with a thermochromic material which turns color when a specific heat is achieved. The material can be patterned such that lettering may indicate the words "HOT DOG" for promotional and advertisement value. Conveniently, an aqueous form of the thermochromic agent is ink jet printed into a pattern representing words of interest. The polymerizable dual chain lipid BRONCO was suspended in water and pre-polymerize with ultraviolet light (254 nm) at room temperature to a dark blue ink color. The polymer solution was printed on the side of a retail available hot dog (Hormel or Kraft). The chromic agent can also be printed on the meat product cellulosic casing prior to filling the casing with processed meats and fillers. Casings are typically extruded, processed, and dried prior to filling. Printing on the unfilled casing provides the advantage of printing on a dry solid surface using high speed printing and drying methods with out effecting the foodstuff. Printing on the casing can involve ink jet printing, pad printing, masking, spraying, silk screening, extrusion or the like.

Brownie Mix: Brownie mixes were prepared by incorporating a blue thermochromic agent that changes to bright orange upon heating. Upon preparation of the brownie mix according to the manufacturer's directions and baking, the dark brown mix became bright orange. The thermochromic agent thus served as both an entertaining color change component of the mix, and as an indicator that the brownies were done and ready to be removed from the oven.

Embedded food bar codes: Embedded thermochromic bar codes produced directly on the side of a pre-baked ham cut. A thermochromic bar code allows a standard bar code and bare code reader to be used as a thermometer device. An alcoholic solution containing TDA/PDA (described above) was sprayed locally on the side of a 1 pound piece of pre-cooked ham (Hormel Company). The ham surface was prepared by damp drying a 1×2 inch region. The region was sprayed at a distance of 3 inches using an airbrush as described above. An ultraviolet transmissive photomask with a negative bar code pattern was prepared using a black film thermal transfer printer (Brother) and 8.5×11 inch sheet of 4 mil thick clear polyethylene sheet. The bar code photomask, sized to 0.75 by 1.5 inch, was placed directly over the sprayed region of TDA/PDA. The bars in the code were transmissive to ultraviolet light (254 nm). The bars were selectively exposed using a light shield over certain bars while others were exposed. This method allowed some bars to be polymerized for 100% more time than others did so that the lesser exposed bars would change color at lower temperatures (125° F.) and the more highly exposed bars would change color at higher temperatures (170° F.). The differential temperatures were set so that a bar code reader could read while ham was hot so that the bar code scanner could interpret the disappearance of certain bars (due to the dark blue to red color transition during heating) as being a different code than when it started. The scanner information was converted digitally using a standard computer so that the corresponding computer output could indicate the actual temperature.

3. Decoration of Ingestibles

Thermochromic cereals: A low temperature reversible thermochrome can be prepared in a versatile polyethylene glycol coating. A coating solution containing the polymerizable monomer N-ethanol-hexadeca-5,7-diyneamide (100 mg/ml) 3,350 molecular weight polyethylene glycol (750 mg/ml) was made in an ethanol (absolute) by warming to 120° F. and mixing. The viscous solution remained clear above 100° F. The coating solution is slightly viscous and easily applied to a food surface by blotting, painting, or spraying. Both the N-ethanol-hexadeca-5,7-diyneamide and polyethylene glycol crystallize from solution upon cooling to room temperature and solvent evaporation. Foods cereals such as Kellogg's Frosted Miniwheats were coated by painting with a thin coat and allowed to dry at room temperature for 2 hours. The resulting coat dried to a hard wax-like appearance. The N-ethanolhexadeca-5,7-diyneamide was polymerized using a hand-held ultraviolet lamp (254 nm, 6 inch distance) for a total exposure time of 1 minute. The resulting layer became strongly magenta at room temperature 68 72° F.), bright red/orange at increasing temperature (85-95° F.), and dark blue/purple when chilled (35-55° F.). The color change is completely reversible as long as the upper temperature level is maintained below 130° F. The coated cereal pieces turn from a bright magenta/red to dark purple/blue when cold milk is poured over their surface (42° F.). The dark purple/blue color remains as long as the milk remains cold. The color is thermochromically reversible through-hot and cold cycles.

Processed thin sliced cheese: Pre-packaged thin sliced cheese can be printed with the aqueous solution of the thermochromic agent. The solution can be pre-polymerized or in a monomeric form which can be polymerized after printing. The thermochromic agent is absorbed to the cheese surface upon brief drying causing a strong bonding to occur between the thermochromic agent and the surface of the cheese.

A pattern of the American flag was produced on the surface of a thin slice of American cheese (Kraft 2% Milk Reduced Fat Milk Singles). The pattern was painted using a thin brush and a dark blue solution of pre-polymerized BRONCO. The pattern was allowed to dry at room temperature for 5 minutes and the cheese repackaged for storage.

The flag-painted slice of cheese was placed on a hamburger while the burger was cooking on a grill. Within 2-3 minutes, the cheese began to melt. During heating and melting, the dark blue flag pattern became bright red. The flag pattern also started to flow and contort as the cheese melted and flowed. The flow process gave rise to an interesting effect, simulating a waving and moving flag.

Thermochromic sugars, salts, spices, cheese powders, grated cheese, and shredded cheese: An ethanol coating solution was prepared with ethanol (Spectrum Chemicals Inc.) containing 150 mg/ml 10,12-tricosadiynoic acid (GFS Chemicals, Inc.). The solution was warmed to 100° F. to dissolve all of the diacetylenic acid. Twenty grams of sugar, salt, spice (e.g. paprika or mustard seeds), or cheese powder (e.g. Parmesan cheese or powdered cheese from Kraft Macaroni and Cheese mix) were added to a screw cap bottle and saturated with up to 2.5 ml of the ethanolic solution. A powder and solution were shaken and tumbled for 3 minutes to ensure complete coverage of the particles. The solution wetted powders were poured into a Teflon coated dish and tumbled for 10 minutes with a gentle air stream to ensure that all of the ethanol solution was removed. The coated powders were vigorously shaken and exposed to ultraviolet light (hand held lamp, Cole Parmer, Inc. 254 nm) for 5 minutes resulting in the deep-blue appearance of the polydiacetylenic polymer. Once dry, the coated powders could be used immediately.

Thermochromic triggering was accomplished by applying a powder type directly to a heated food type. For example, the chromic agent coated powder cheese was added to a pre-heated/cooked bowl of macaroni. On contact, the dark blue cheese powder turns to a vivid red orange color. Visual effects can be created by first adding a small pile of the treated pile to a hot food. At first the shallow edges turn orange and then the blue pile gradually turns orange with the orange color radiating inward until finally the peak is triggered orange. Alternatively, the coated powder can be sparsely sprinkled on the food such that each grain turns color instantly.

Thermochromic soup crackers: Soup crackers (e.g., Pepperidge Farms Fish Cracker brand or standard soup crackers) were lightly sprayed and wetted with an adhesive food glaze (150 mg/ml water soluble starch dissolved in purified water sprayed with a nebulizer). The lightly wetted surface was tacky to the touch for several minutes prior to drying. While the surface was tacky, the crackers were coated with a thermochromic salt powder as prepare above. The coated salt particles adhered to the cracker surface once the adhesive food glaze dried. The final crackers revealed a blue tint on their surface. The optical density of blue color was regulated by the amount of coated salt applied.

Thermochromic triggering was accomplished by dipping a cracker into a hot bowl of soup. The dark blue tint on the cracker surface turned immediately to a bright orange on contact with the hot liquid. Visual effects were created by dipping the crackers at various depths and angles into the soup.

4. Storage Temperature Condition Indicators

Raw egg holding temperature indicator: Eggs were printed with the alcoholic solution containing MeTDA described above. The monomer solution was spot printed using a porous felt pad saturated with the monomer solution. Printing was conducted while the eggs were held at 40° F. The monomer was allowed to dry for 2 minutes and polymerized at using a hand held ultraviolet lamp (254 nm) at 40° F. The dark blue printed spot held its color on an egg until the egg was raised to between 55 to 65° F. were the dark blue spot became bright red/orange indicate that the egg was exposed to an excessive holding temperature range. Eggs should be kept at refrigerator temperature during storage due to the potential contamination of *Salmonella* and the possibility of cell replication at above refrigerator temperatures.

Example 4

Mechanical Stress-Triggered Chromic Change Agents

Candies and cookies possessing mechanically induced color changes: Hard candies such as jaw breakers, M & M's, hard coated gum pieces, hard icing coated cookies, or the like were coated with a color change agent that changes color due to mechanical and/or frictional forces applied to the surface with the mechanochromic agent. An ethanol coating solution was prepared with ethanol (Spectrum Chemicals, Inc.) containing 200 mg/ml 10,12-octadecadlynoic acid (GFS Chemicals, Inc.). The solution was spray coated onto candy or cookie surfaces using a conventional air brush system. The coating can be applied either while the candy or cookie surface is stationary or tumbling. Once an even coat has been applied, the surfaces are allowed to dry at room temperature of 30 minutes. The coated surfaces are polymerized using an ultraviolet light (hand held lamp, Cole Parmer Inc. 254 nm) for 5 minutes resulting in the blue appearance of the polydiacetylenic polymer.

Candy and cookie surfaces coated with the blue polydiacetylene layer are changed to a red/orange color by rubbing surfaces together, rubbing with a finger or finger nail, or rubbing with a compatible hard surface. Surfaces with temperature insulative properties such as finger nails, napkins, wood sticks, paper dowels, plastic sticks or the like are superior for inducing the color change compared with metal or glass surfaces which have heat conductive surfaces. Patterns, messages, and graphical images can be created on the mechanochromic surface by localized rubbing without changing the color of an adjacent region of the blue mechanochromic agent.

Mechanochromic tooth paste: A ratio of 10 g Crest Tooth Paste with 1 gram pre-polymerize flakes of 5,7-hexadecadiynoic was mixed at room temperature to become a blue paste containing small blue particles of the diacetylenic polymer. 5,7-hexadecadiynoic acid (GFS Chemicals, Inc.) flake-like crystals were polymerized to a dark blue tint using a hand-held ultraviolet lamp (Cole Parmer inc.) for 3 minutes. The flakes were agitated during the process to ensure complete polymerization. The dark blue flakes were added to tooth paste at room temperature and mixed thoroughly. The final formulation was stable at room temperature. The mechanochromic tooth paste turned form a dark blue paste to a pink/purple color when the tooth paste was abraded back and forth with a standard tooth brush (medium bristles) for 2-3 minutes.

Touch Sensitive Rice Krispie® Treats: Retail Rice Krispie Treats (Kellogg Company) were air brush spray coated using the method described above and an alcoholic solution of MePDA prepared as described above. The Rice Krispie Treats surfaces were inclined at 30 degrees on an open tray and sprayed at a distance of 4 inches using a moderate stream flow from the airbrush. The coatings were allowed to dry for 5 minutes at 65 g. Pattern coating was accomplished using an open letter stencil and spraying just beyond the outline of the stencil. Polymerization was accomplished using a hand held ultraviolet lamp (254 nm) moved back and forth over the surface for 5 seconds at a distance of 3 inches. The surface immediately became dark blue and could be made to change color to a bright red/orange by finger touch, breathing on the surface, or biting into the surface.

Example 5

Combined Temperature-Mechanical Stress-Triggered Chromic Change Agents

Combined photochromic thermochromic—mechanochromic cookies: An ethanol solution was prepared with ethanol (Spectrum Chemicals, Inc.) containing 150 mg/ml 10,12-tricosadiynoic acid and 15 mg/ml 10,12-pentacosadiynoic acid. The solution was warmed to 100° F. to dissolve all of the diacetylenic acid. The solution was loaded into an emptied, cleaned, and dried ink jet cartridge (Hewlett Packard HP 51629A). The cartridge was placed in an ink jet printer (Hewlett Packard, Deskwriter 680C). The printing room and printing components were maintained at a temperature of 95° F. to ensure that the ethanol printing solution remained soluble. Edible laminates (Kopykake Inc., Torrance, Calif.) were printed using standard graphics programs and interfaces.

Graphical images were printed on the laminate and then adhered to the surface of cookies. The cookies were place in the sun or exposed to a hand held ultraviolet light source (Cole Parmer, Inc.). The graphical images appeared exactly as they were printed upon exposure. The graphical images became visible within minutes in sun light (peak intensity at 12:00 noon during the spring time in California). The color became progressively darker with continued exposure up to hours.

The dark blue images printed on the cookies could be subsequently triggered to a bright red upon heating the cookie or dipping it in hot liquid (milk heated to 130° F.). Variations ultraviolet activated color development times and thermochromic temperature transitions can be achieved by modifying the polydiacetylene structure utilized.

The blue polydiacetylenic images on the cookie surface can also undergo a mechanochromic transition to a red/orange color by mildly rubbing the image/cookie surface. The mechanochromic effect is highly localized to the specific are being contacted. The image can be graphically altered by localized rubbing to achieve different graphical effects based on multiple colors (e.g. the background cookie color, the blue form of the polymer, and the red/orange form of the polymer).

Example 6

Combined Temperature-Chemical Triggered Chromic Change Agents

Chromic change liquid beverage with dual function: An aqueous suspension 100 mg/ml of N-ethanol-hexadeca-5,7-diyneamide was prepared using ultrasonication and lecithin as an emulsifier. One gram N-ethanol-hexadeca-5,7-diyneamide (prepared as described in this patent) and 1 gram egg lecithin (Sigma Chemicals, Inc.) were added to a glass beaker along with 30 ml filtered water and sonicated with a high power probe sonicator (Cole Parmer, Inc.) for 10 minutes at 130° F. Homogeneous suspension formation required agitation and mixing. The final suspension was milky white. The suspension was allowed to cool to room temperature and left to stand 24 hours. The suspension was dispersed by mixing or agitation. Five ml of the solution was added to a shallow dish and exposed to ultraviolet light (hand held lamp, Cole Parmer, Inc. 254 nm) for 5 minutes (with continual mixing and agitation) resulting in the deep magenta appearance of the polydiacetylenic polymer (room temperature). The magenta color chromic solution could be diluted with water or kept concentrated.

For thermochromic conversion, a 5 fold diluted solution of the chromic solution (purified water) was poured over crushed ice in a clear glass. The color immediately changed to a dark purple/blue color upon chilling. The solution color was thermochromically reversible when rewarmed to room temperature and subsequently chilled back to near freezing temperatures. Temperature cycling could be repeated numerous times.

For chemochromic conversion the chilled purple/blue chromic solution can be further changed to a bright pink/orange color by the addition of alcohol (chilled or ambient in temperature). Addition of an increasing concentration of alcohol caused the purple/blue color to progressively turn irreversibly to a pink/orange color. When greater than 50% alcohol (volume/volume water/alcohol) is added the solution becomes completely pink/orange. The system serves as a means to detect the presence of polar solvents such as alcohol or acetone.

Example 7

Moisture Triggered Chromic Change Agents

Hydrochromic ingestible sugar, sprinkles, nonpareil and salt powders: An ethanol coating solution was prepared with ethanol (Spectrum Chemicals, Inc.) containing 130 mg/ml 4,6-decadiyne-1,10-diol (GFS Chemicals, inc.). 20 grams sugar or salt powder were added to a screw cap bottle and saturated with up to 2.5 ml of the ethanolic solution. A powder and solution were shaken and tumbled for 5 minutes to ensure complete coverage of the particles. The solution wetted powders were poured into a Teflon coated dish and tumbled for 10 minutes with a gentle air stream to ensure that all of the ethanol solution was removed and the coated powder consisted of a in a fine grain mesh with out clumps. The coated powders were vigorously shaken and exposed to ultraviolet light (hand held lamp, Cole Parmer, inc. 254 nm) for 5 minutes resulting in the deep blue/purple appearance of the polydiacetylenic polymer. Once polymerized the coated powders could be used immediately. Hydrochromic powders were stored at room temperature of below in sealed jars and desiccants.

Hydrochromic powders were adhered to food surfaces such as cereals, cookies, crackers or any other food type intended to come in contact with an aqueous medium. For example, a hydrochromic sugar can be coated on the surface of a cookie intended of dipping in milk. The visual appearance of the blue/purple sugar powder can be enhanced by pre-coating the cookie with a bright white royal hard sugar icing. Immediately prior to the final drying stage of icing, a hydrochromic sugar powder can be layered on to the icing surface. Residual water in the cookie icing will not change the outward surface color of the hydrochromic sugar powder as long as the water content in the icing is minimized and the grains do not wet. A gentle air stream over the coating facilitates drying. Alternatively a tacky adhering glaze can be used for coating the food surface with the powder. The blue/purple powder can be coated at a density practical for viewing.

Hydrochromic triggering is accomplished by dipping a coated cookie into chilled milk (liquid at room temperature or as low as 45° F.). The blue/purple color changes to a bright orange on wetting. The color change within seconds using liquids at near room temperature and has a delayed effect over 30 to 90 seconds using liquids well below room temperature (45° F. to 55° F.).

Powders with very thin coats of the hydrochromic agent change color more rapidly than coatings that are thick since thicker coatings are restrictive in letting water rapidly intercalate into the chromic agent's interstitial layer. The visual effect of hydrochromic color change can be regulated depending on the food type of interest. Hydrochromic coatings can also find use as integrated indicators that foods have been properly sealed form moisture there by ensuring freshness and dryness during storage.

It is evident from the above description and results that by using a thermochromic agent that undergoes a color change, many applications accrue. The thermochromic agent may be applied to a wide variety of ingestibles in a wide variety of manners, incorporated into the ingestible, particularly liquids, or associated with the ingestible, such as on packaging materials. The thermochromic composition can be used to ensure that an ingestible has been stored safely, that it has been cooked to a desirable temperature, that it has cooled to a desired temperature, or solely for marketing or entertainment purposes. Exposure of ingestibles comprising moisture-sensitive chromic change agents to solutions or moist atmospheres can provide entertaining color changes or reveal text or imaged based messages. Mechanical stress-triggered chromic change agents that change color due to mechanical and/or frictional force may be incorporated into a variety of ingestibles that are rubbed, scratched, chewed, compressed, or the like, and find particular use in toothpastes and touch-sensitive ingestibles. Ingestibles incorporating a number of different chromic change agent combinations are provided that can reveal different text messages or images and sequentially-displayed text or images based on the types of treatments to which the ingestible is exposed. These messages may serve to direct the user to the next step in a preparation process, reveal hidden messages, and serve as diagnostic indicators. The compositions are physiologically safe and may be modified to be appropriate as to a particular temperature transition and compatible with the ingestible.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for effecting at least one color change in or on an edible ingestible, said method comprising;
    incorporating into or onto said edible ingestible a diacetylenic compound that undergoes said at least one color change when subjected to at least one environmental change to produce an edible ingestible comprising said diacetylenic compound, wherein said diacetylenic compound is physiologically acceptable and associated with the edible ingestible so as to be ingested; and
    subjecting said edible ingestible to said at least one environmental change, whereby said at least one environmental change triggers said at least one color change on said edible ingestible.

2. The method according to claim 1, in which said at least one environmental change is selected from the group consisting of change in temperature, pH, illumination, chemical exposure, biochemical exposure, mechanical stress, ionization, protonation, hydrogen bonding, state of hydration, and state of solvation.

3. The method according to claim 1, wherein said edible ingestible comprises a food or medicament.

4. The method according to claim 1, wherein said at least one color change forms at least one pattern on said edible ingestible.

5. The method according to claim 4, wherein said at least one pattern is selected from the group consisting of text, characters, images, symbols, branding identities, trademarks, messages, icons, logos, artistic designs and decorative designs.

6. The method according to claim 5, wherein said at least one pattern is visualized sequentially by propagating a color change along a surface.

7. The method according to claim 1, wherein said incorporating of said diacetylenic compound is into said edible ingestible.

8. The method according to claim 1, wherein said diacetylenic compound is suffused through the edible ingestible.

9. The method according to claim 1, wherein said diacetylenic compound partially penetrates the edible ingestible.

10. The method according to claim 1, wherein said diacetylenic compound coats the ingestible.

11. The method according to claim 1, wherein said at least one color change is an intrinsic color change.

12. The method according to claim 1, wherein said at least one color change is reversible.

13. The method according to claim 1, wherein said at least one color change is irreversible.

14. A method comprising ingesting an edible ingestible comprising a diacetylenic compound that undergoes at least one color change when subjected to at least one environmental change, wherein said diacetylenic compound is physiologically acceptable and associated with the edible ingestible so as to be ingested.

15. The method according to claim 14, in which said at least one environmental change is selected from the group consisting of change in temperature, pH, illumination, chemical exposure, biochemical exposure, mechanical stress, ionization, protonation, hydrogen bonding, state of hydration, and state of solvation.

16. The method according to claim 14, wherein said edible ingestible comprises a food or medicament.

17. The method according to claim 14, wherein said at least one color change forms at least one pattern on said edible ingestible.

18. The method according to claim 17, wherein said at least one pattern is selected from the group consisting of text, characters, images, symbols, branding identities, trademarks, messages, icons, logos, artistic designs and decorative designs.

19. The method according to claim 18, wherein said at least one pattern is visualized sequentially by propagating a color change along a surface.

20. The method according to claim 14, wherein said diacetylenic compound is inside said edible ingestible.

21. The method according to claim 14, wherein said diacetylenic compound is suffused through said edible ingestible.

22. The method according to claim 14, wherein said diacetylenic compound partially penetrates said edible ingestible.

23. The method according to claim 14, wherein said diacetylenic compound coats said ingestible.

24. The method according to claim 14, wherein said at least one color change is an intrinsic color change.

25. The method according to claim 14, wherein said at least one color change is reversible.

26. The method according to claim 14, wherein said at least one color change is irreversible.

* * * * *